(12) United States Patent
Folger et al.

(10) Patent No.: US 10,398,705 B2
(45) Date of Patent: Sep. 3, 2019

(54) PHARMACEUTICAL TABLET FORMULATION FOR THE VETERINARY MEDICAL SECTOR, METHOD OF PRODUCTION AND USE THEREOF

(71) Applicant: BOEHRINGER INGELHEIM VETMEDICA GMBH, Ingelheim am Rhein (DE)

(72) Inventors: Martin Folger, Ingelheim am Rhein (DE); Ragna Hoffmann, Biberach an der Riss (DE); Florent Robin, Brussels (BE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 90 days.

(21) Appl. No.: 14/384,210

(22) PCT Filed: Mar. 14, 2013

(86) PCT No.: PCT/EP2013/055310
§ 371 (c)(1),
(2) Date: Sep. 10, 2014

(87) PCT Pub. No.: WO2013/135852
PCT Pub. Date: Sep. 19, 2013

(65) Prior Publication Data
US 2015/0064249 A1  Mar. 5, 2015

(30) Foreign Application Priority Data
Mar. 15, 2012  (EP) .................................. 12159629

(51) Int. Cl.
*A61K 9/16* (2006.01)
*A61K 9/20* (2006.01)
(Continued)

(52) U.S. Cl.
CPC ............ *A61K 31/55* (2013.01); *A61K 9/0056* (2013.01); *A61K 9/1676* (2013.01);
(Continued)

(58) Field of Classification Search
CPC ...... A61K 31/50; A61K 31/501; A61K 31/55; A61K 9/0056
See application file for complete search history.

(56) References Cited

U.S. PATENT DOCUMENTS 3,574,859 A  4/1971 Kosti
3,822,349 A  7/1974 Kosti
(Continued)

FOREIGN PATENT DOCUMENTS

AU  2012101682 A4  1/2013
CA  950833 A1  7/1974
(Continued)

OTHER PUBLICATIONS

Vromans et al Densification properties and compactibility of mixtures of pharmaceutical excipients with and without magnesium stearate . International Journal of pharmaceutics, 46, 183-192. 1988.*
(Continued)

*Primary Examiner* — Lakshmi S Channavajjala
(74) *Attorney, Agent, or Firm* — Judy Jarecki-Black

(57) ABSTRACT

The invention is directed to a pharmaceutical tablet formulation for the veterinary medical sector containing an instable ACE inhibitor or a pharmaceutically acceptable salt thereof as a first pharmaceutically active substance, and pimobendan or a pharmaceutically acceptable salt thereof as a second pharmaceutically active substance, comprising granules which contain carrier core particles coated with at least one layer wherein the first pharmaceutically active substance is present, the granules being embedded in a tablet (Continued)

matrix wherein the second pharmaceutically active substance is present. It is provided a "fixed-dose-combination" which allows to ease the treatment and administration of the medication, improves the medication compliance by reducing the pill burden to the animal holder and enables the better observation of and adherence to the therapy by decreasing the number of tablets to be administered. The lower number of tablets leads to a lower treatment failure rate, minimizes dosage mistakes and avoids confusions by false dose intake and slower development of resistance.

21 Claims, 3 Drawing Sheets

(51) Int. Cl.
  *A61K 31/55* (2006.01)
  *A61K 31/501* (2006.01)
  *A61K 9/50* (2006.01)
  *A61K 9/00* (2006.01)
(52) U.S. Cl.
  CPC .......... *A61K 9/2077* (2013.01); *A61K 9/2081* (2013.01); *A61K 9/5078* (2013.01); *A61K 31/501* (2013.01); *A61K 9/5026* (2013.01)

(56) References Cited

U.S. PATENT DOCUMENTS

| | | | |
|---|---|---|---|
| 3,832,460 A | 8/1974 | Kosti | |
| 3,839,522 A | 10/1974 | Kosti | |
| 3,950,333 A | 4/1976 | Durant et al. | |
| 4,128,658 A | 12/1978 | Price et al. | |
| 4,256,743 A | 3/1981 | Goldhaber | |
| 4,283,400 A | 8/1981 | von Bittera et al. | |
| 4,283,408 A | 8/1981 | Hirata et al. | |
| 4,293,557 A | 10/1981 | Shibata et al. | |
| 4,361,563 A | 11/1982 | Austel et al. | |
| 4,375,547 A | 3/1983 | Pioch | |
| 4,386,099 A | 5/1983 | Cereda et al. | |
| 4,427,648 A | 1/1984 | Brickl et al. | |
| 4,569,837 A | 2/1986 | Suzuki et al. | |
| 4,585,790 A | 4/1986 | Padfield et al. | |
| 4,596,705 A | 6/1986 | Schepky et al. | |
| 4,654,342 A | 3/1987 | Slater | |
| 4,704,284 A | 11/1987 | Beatty et al. | |
| 4,732,915 A | 3/1988 | Ayer et al. | |
| 4,851,226 A | 7/1989 | Julian et al. | |
| 4,865,851 A | 9/1989 | James et al. | |
| 4,868,182 A | 9/1989 | Dage | |
| 4,906,628 A | 3/1990 | Coates | |
| 4,933,182 A | 6/1990 | Higashi et al. | |
| 4,954,501 A | 9/1990 | Herter et al. | |
| 4,973,469 A | 11/1990 | Mulligan et al. | |
| 5,024,998 A | 6/1991 | Bodor | |
| 5,151,420 A | 9/1992 | Backstrom et al. | |
| 5,188,836 A * | 2/1993 | Muhammad | A61K 9/5078 424/439 |
| 5,364,646 A | 11/1994 | Gruber et al. | |
| 5,569,657 A | 10/1996 | Nore et al. | |
| 5,571,533 A | 11/1996 | Santus et al. | |
| 6,162,802 A | 12/2000 | Papa et al. | |
| 6,407,079 B1 | 6/2002 | Muller et al. | |
| 6,476,078 B1 | 11/2002 | Jerussi et al. | |
| 6,669,955 B2 * | 12/2003 | Chungi | A61K 9/2077 424/451 |
| 6,713,487 B2 | 3/2004 | Yu et al. | |
| 7,262,165 B2 | 8/2007 | Lindenblatt et al. | |
| 8,409,612 B1 | 4/2013 | Criere et al. | |
| 8,846,679 B2 * | 9/2014 | Folger | A61K 31/501 514/252.06 |
| 8,980,894 B2 | 3/2015 | Daemmgen et al. | |
| 2003/0059471 A1 | 3/2003 | Compton et al. | |
| 2003/0162835 A1 | 8/2003 | Staniforth et al. | |
| 2003/0165565 A1 * | 9/2003 | Mehta | A61K 9/5078 424/468 |
| 2003/0190343 A1 | 10/2003 | Thombre et al. | |
| 2003/0212114 A1 | 11/2003 | Sato | |
| 2004/0037869 A1 | 2/2004 | Cleverly et al. | |
| 2004/0152664 A1 | 8/2004 | Chang et al. | |
| 2004/0157887 A1 | 8/2004 | Whittle et al. | |
| 2005/0095293 A1 | 5/2005 | Brauns et al. | |
| 2005/0203097 A1 | 9/2005 | Folger et al. | |
| 2005/0239692 A1 | 10/2005 | Lindenblatt et al. | |
| 2007/0112010 A1 | 5/2007 | Kleeman et al. | |
| 2008/0207629 A1 | 8/2008 | Folger et al. | |
| 2009/0082282 A1 | 3/2009 | Daemmgen et al. | |
| 2010/0035889 A1 | 2/2010 | Daemmgen et al. | |
| 2010/0166857 A1 * | 7/2010 | Yan | A61K 9/1676 424/465 |
| 2010/0183718 A1 | 7/2010 | Ovaert et al. | |
| 2010/0273807 A1 | 10/2010 | Kleeman et al. | |
| 2011/0028457 A1 | 2/2011 | Roewer et al. | |
| 2011/0189283 A1 | 8/2011 | Derrieu et al. | |
| 2011/0251208 A1 | 10/2011 | Daemmgen et al. | |
| 2011/0318420 A1 | 12/2011 | Hu et al. | |
| 2012/0148640 A1 | 6/2012 | Folger et al. | |
| 2012/0308662 A1 | 12/2012 | Konishi et al. | |
| 2013/0115301 A1 | 5/2013 | Bele et al. | |
| 2013/0203690 A1 | 8/2013 | Daemmgen et al. | |
| 2014/0155338 A1 | 6/2014 | Daemmgen et al. | |
| 2014/0235648 A1 | 8/2014 | Folger et al. | |
| 2015/0025082 A1 | 1/2015 | Aven et al. | |
| 2015/0150820 A1 * | 6/2015 | Laczay | A61K 9/1641 424/489 |
| 2016/0038420 A1 | 2/2016 | Brunel et al. | |
| 2017/0290829 A1 | 10/2017 | Schummer et al. | |

FOREIGN PATENT DOCUMENTS

| | | |
|---|---|---|
| CA | 1222697 A1 | 6/1987 |
| CA | 2034569 A1 | 7/1991 |
| CA | 1336498 C | 8/1995 |
| CN | 1662250 A | 8/2005 |
| CN | 1702243 A | 11/2005 |
| DE | 3728244 A1 | 3/1989 |
| DE | 4001623 A1 | 7/1991 |
| EP | 0241179 A1 | 10/1987 |
| EP | 0256566 A1 | 2/1988 |
| EP | 0268146 A1 | 5/1988 |
| EP | 0306846 A2 | 3/1989 |
| EP | 0330052 A2 | 8/1989 |
| EP | 0335545 A2 | 10/1989 |
| EP | 0349657 A1 | 1/1990 |
| EP | 439030 A2 | 7/1991 |
| EP | 1123703 A1 | 8/2001 |
| EP | 1247456 A2 | 10/2002 |
| EP | 1260215 A1 | 11/2002 |
| EP | 1579862 A1 | 9/2005 |
| EP | 1903039 A1 | 3/2008 |
| EP | 14900307 B1 | 3/2008 |
| EP | 1920785 A1 | 5/2008 |
| EP | 2338493 A1 | 6/2011 |
| EP | 3034071 A1 | 6/2016 |
| FR | 2350105 A1 | 12/1977 |
| GB | 1045031 A | 10/1966 |
| GB | 2228004 A | 8/1990 |
| GB | 2394660 A | 5/2004 |
| JP | 61500788 A | 4/1986 |
| JP | H029825 A | 1/1990 |
| JP | H0489428 A | 3/1992 |
| JP | H0570612 A | 3/1993 |
| JP | H11228302 A | 8/1999 |
| JP | 2005-281283 A | 10/2005 |
| JP | 2005281283 A | 10/2005 |
| JP | 2007191419 A | 8/2007 |
| JP | 2008504308 A | 2/2008 |
| JP | 2011157390 A | 8/2011 |
| JP | 2012533595 A | 12/2012 |
| JP | 2013006798 A | 1/2013 |
| JP | 2013503113 A | 1/2013 |
| WO | 1985002767 A1 | 7/1985 |

(56) References Cited

FOREIGN PATENT DOCUMENTS

| | | |
|---|---|---|
| WO | 1989004178 A1 | 5/1989 |
| WO | 1995031963 A1 | 11/1995 |
| WO | 0012137 A1 | 3/2000 |
| WO | 2000069414 A2 | 11/2000 |
| WO | 2001035925 A1 | 5/2001 |
| WO | 2001064190 A1 | 9/2001 |
| WO | 2001097861 A2 | 12/2001 |
| WO | 0245693 A1 | 6/2002 |
| WO | 2002049646 A1 | 6/2002 |
| WO | 2003012030 A2 | 2/2003 |
| WO | 03072141 A1 | 9/2003 |
| WO | 2003074032 A1 | 9/2003 |
| WO | 2003075895 A1 | 9/2003 |
| WO | 20030075842 A1 | 9/2003 |
| WO | 2003097067 A1 | 11/2003 |
| WO | 2003099194 A2 | 12/2003 |
| WO | 2004000317 A1 | 12/2003 |
| WO | 2004000344 A1 | 12/2003 |
| WO | 2004016252 A1 | 2/2004 |
| WO | 2004033444 A1 | 4/2004 |
| WO | 2004050657 A2 | 6/2004 |
| WO | 2004058726 A2 | 7/2004 |
| WO | 2004060353 A1 | 7/2004 |
| WO | 2004089418 A1 | 10/2004 |
| WO | 2005035505 A2 | 4/2005 |
| WO | 2005084647 A1 | 9/2005 |
| WO | 2005092343 A1 | 10/2005 |
| WO | 2005107756 A1 | 11/2005 |
| WO | 2005117911 A2 | 12/2005 |
| WO | 2006000229 A2 | 1/2006 |
| WO | 2006022562 A1 | 3/2006 |
| WO | 2006060122 A2 | 6/2006 |
| WO | 2006060127 A2 | 6/2006 |
| WO | 20060085208 A1 | 8/2006 |
| WO | 2007036671 A2 | 4/2007 |
| WO | 2007038796 A1 | 4/2007 |
| WO | 2007054514 A2 | 5/2007 |
| WO | 2007112274 A2 | 10/2007 |
| WO | 2007128749 A1 | 11/2007 |
| WO | 2008055871 A1 | 5/2008 |
| WO | 20080095263 A1 | 8/2008 |
| WO | 2009060226 A1 | 5/2009 |
| WO | 2010010257 A2 | 1/2010 |
| WO | 2010055119 A2 | 5/2010 |
| WO | 2010060874 A1 | 6/2010 |
| WO | 20100097501 A1 | 9/2010 |
| WO | 2011009818 A1 | 1/2011 |
| WO | 2011042463 A2 | 4/2011 |
| WO | 2011076738 A1 | 6/2011 |
| WO | 20110111066 A1 | 9/2011 |
| WO | 2013024023 A1 | 2/2013 |
| WO | 2013135852 A1 | 9/2013 |
| WO | 2013164473 A1 | 11/2013 |
| WO | 2013170317 A1 | 11/2013 |
| WO | 2014136035 A1 | 9/2014 |
| WO | 2017174571 A1 | 10/2017 |

OTHER PUBLICATIONS

Fox et al. Bradykinin-evoked sensitization of airway sensory nerves: A mechanism for ACE-inhibitore cough. 1996 Nature Medicine, Jul. 1996, vol. 2, No. 7, pp. 814-817.*

Abstract in English for JPH0489428, 1992.

Ash et al., "Receptor Mediating Some Actions of Histamine". British Journal of Pharmacology and Chemotherapy, vol. 27, No. 2, Aug. 1996, pp. 427-439.

Black et al., "Definition and Antagonism of Histamine H2-receptors". Nature, vol. 236, Apr. 1972, pp. 385-390.

Dews et al., "The Antihistamine Substance 2786 R.P." British Journal of Pharmacology, vol. 1, 1946, pp. 278-286.

Loew, Earl R., "Gastric Secretion in Dogs Treated with Histamine Antagonist, Thymoxyethyldiethylamine". Experimental Biology and Medicine, vol. 48, No. 1, Oct. 1941, pp. 65-68.

Lantz et al., "Stability of nizatidine in extemporaneous oral liquid preparations". American Journal of Hospital Pharmacy, vol. 47, No. 12, Dec. 1990, pp. 2716-2719.

Nakamoto et al., "The role of ascorbic acid deficiency in human gingivitis—a new hypothesis". Journal of Theoretical Biology, vol. 108, No. 2, May 1984, pp. 163-171.

Pernsteiner et al., "Effect of Topical Application of Phenylephrine Hydrochloride on Hyperplastic Gingivitis". Journal of Periodontology, vol. 48, No. 8, Aug. 1977, pp. 473-477.

Trendelenburg, U. "The Action of Histamine and 5-Hydroxytryptamine on Isolated Mammalian Atria". The Journal of Pharmacology and Experimental Therapeutics, vol. 130, No. 4, Dec. 1960, pp. 450-460.

Thiel et al., "Content uniformity of microdose tablets (dosage 1 μg-10 mg) produced by fluid bed granulation of interactive mixtures". Journal of Pharmacy and Pharmacology, vol. 38, 1986, pp. 335-343.

Petit et al., "VETMEDIN® 1.25 mg, VETMEDIN® 5 mg, Chewable tablets, Inodilator (pimobendan) tablet for dogs". Dictionary of Veterinary Drugs and Animal Health Products Marketed in France, 16th Edition, Les Editions du Point Vétérinaire, 2011, pp. 1658-1661.

"Vetmedin®—1,25 mg appetizing tablets for dogs Veterinary use". Summary of Product Characteristics, SCS Boehringer Ingelheim Comm. V, Mar. 25, 2009, pp. 1-4.

"Rimadyl F 50 mg". Summary of Product Characteristics, Zoetis France, May 15, 2013, pp. 1-4.

Hemati et al., "Fluidized bed coating and granulation: influence of process-related variables and physicochemical properties on the growth kinetics". Powder Technology, vol. 13, 2002, pp. 18-34.

Fox, Philip R., "Hypertrophic Cardiomyopathy. Clinical and Pathologic Correlates". Journal of Veterinary Cardiology, vol. 5, No. 2, Nov. 2003, pp. 39-45.

Fuentes, et al., "A Double-Blind, Randomized, Placebo-Controlled Study of Pimobendan in Dogs with Dilated Cardiomyopathy," Journal of Veterinary Internal Medicine, vol. 16, 2002, pp. 255-261.

Fujino et al., "Differential Effects of d- and l-Pimobendan on Cardia Myofilament Calcium Sensitivity[1]". The Journal of Pharmacology and Experimental Therapeutics, vol. 247, No. 2, 1988, pp. 519-523.

Goineau et al., "Cardiomyopathic Syrian Hamster as a Model of Congestive Heart Failure". Current Protocols in Pharmacology, Supp. 42, Unit 5.50, John Wiley & Sons, Inc., Sep. 2008, 12 pages.

Groban, Leanne, "Diastolic Dysfunction in the Older Heart". Journal of Cardiothoracic and Vascular Anesthesia, vol. 19, No. 2, Apr. 2005, pp. 228-236.

Gwathmey et al., "Abnormal Intracellular Calcium Handling in Myocardium From Patients With End-Stage Heart Failure". Circulation Research, vol. 61, No. 1, 1987, pp. 70-76.

Hasenfuss et al., "Influence of the calcium-sensitizer UDCG-115 on hemodynamics and myocardial energetics in patients with idiopathic dilated cardiomyopathy. Comparison with nitroprusside". Basic Research Cardiology, vol. 84, No. 1, 1989, pp. 225-233.

Hauf et al., "Acute and Long-Term Hemodynamic Effects of Pimobendan (UD-CG 115 BS) in Comparison with Captopril". Journal of Cardiovascular Pharmacology, vol. 15, Supp. 2, 1989, pp. S49-S56.

Häggstrom et al., "Effect of Pimobendan or Benazepril Hydrochloride on Survival Times in Dogs with Congestive Heart Failure Caused by Naturally Occurring Myxomatous Mitral Valve Disease: The QUEST Study". Journal of Veterinary Internal Medicine, vol. 22, 2008, pp. 1124-1135.

Häggstrom et al., "Longitudinal Analysis of Quality of Life, Clinical, Radiographic, Echocardiographic, and Laboratory Variables in Dogs with Myxomatous Mitral Valve Disease Rexceiving Pimobendan or Benazepril: The QUEST Study". Journal of Veterinary Internal Medicine, 2013, pp. 1-11.

Häggström et al., "Effects of long-term treatment with enalapril or hydralazine on the renin-angiotension-aldosterone system and fluid balance in dogs with naturally acquired mitral valve regurgitation". American Journal of Veterinary Research, vol. 57, No. 11, Nov. 1996, pp. 1645-1662.

(56) References Cited

OTHER PUBLICATIONS

Häggström et al., "New insights into degenerative mitral valve disease in dogs". Veterinary Clinics Small Animal Practice, vol. 34, 2004, pp. 1209-1226.
International Search Report and Written Opinion for PCT/EP2013/055310 dated Jun. 5, 2013.
Iwasaki et al., "Pimobendan Inhibits the Production of Proinflammatory Cytokines and Gene Expression of Inducible Nitric Oxide Synthase in a Murine Model of Viral Myocarditis". Journal of the American College of Cardiology, vol. 33, No. 5, 1999, pp. 1400-1407.
Jain et al., "Effects of Milrinone on Left Ventricular Remodeling After Acute Myocardial Infarction". Circulation, vol. 84, No. 2, Aug. 1991, pp. 798-804.
Kashem et al., "CardioClasp: A New Passive Device to Reshape Cardiac Enlargement". ASAIO Journal, vol. 48, No. 3, 2002, pp. 253-259.
Kato et al., "Clinical Evaluation of Pimobendan (UD-CG115BS) for Chronic Heart Failure—A Multicentre Placebo-Controlled Double Blind Study". Journal of Clinical Therapeutics & Medicines, vol. 8, No. 6, 1992, pp. 1311-1351.
Kato, Kazuzo, "Clinical Efficacy and Safety of Pimobendan in Treatment of Heart Failure-Experience in Japan". Cardiology, vol. 88, Supp. 2, 1997, pp. 28-36.
Katz et al., "A multicenter, randomized, double-blind, placebo-controlled trial of pimobendan, a new cardiotonic and vasodilator agent, in patients with severe congestive heart failure". American Heart Journal, vol. 123, 1992, pp. 95-103.
Kittleson et al., "The Acute Hemodynamic Effects of Milrinone in Dogs With Severe Idiopathic Myocardial Failure". Journal of Veterinary Medicine, vol. 1, 1987, pp. 121-127.
Koob et al., "Acute Effects of Furosemide on Blood Electrolytes and Hemodynamics in Dogs". Angiology, 1978, pp. 463-472.
Kubo et al., "Beneficial Effects of Pimobendan on Exercise Tolerance and Quality of Life in Patients with Heart Failure. Results of a Multicenter Trial". Circulation, vol. 85, No. 3, Mar. 1992, pp. 942-949.
Kvart et al., "Efficacy of Enalapril for Prevention of Congestive Heart Failure in Dogs with Myxomatous Valve Disease and Asymptomatic Mitral Regurgitation". Journal of Veterinary Internal Medicine, vol. 16, 2002, pp. 80-88.
Lachman et al., "The Theory and Practice of Industrial Pharmacy"., 3rd Edition, Lea & Febiger, Philadelphia, 1986, pp. 58-60.
Lai et al., "Real Time and Noninvasive Monitoring of Dry Powder Blend Homogeneity". AIChE Journal, vol. 47, No. 11, Nov. 2001, pp. 2618-2622.
Lamb et al., "Assessment of the value of the vertebral heart scale in the radiographic diagnosis of cardia disease in dogs". Veterinary Record, vol. 146, 2000, pp. 687-690.
Lewis et al., "Near-Infrared Chemical Imaging for Product and Process Understanding". in Process Analytical Technology, Second Edition, John Wiley & Sons, Ltd., United Kingdom, 2010, pp. 272-276.
Lewis, Alan B., "Clinical Profile and Outcome of Restrictive Cardiomyopathy in Children". American Heart Journal, vol. 123, No. 6, 1992, pp. 1589-1593.
Lip et al., "ABC of heart failure: Aetiology". British Medical Journal, vol. 320, Jan. 2000, pp. 104-107.
Liu et al., "Cardiovascular Pathology: The Role of Cardiovascular Pathology in Practice". Textbook of Canine and Feline Cardiology: Principles and Clinical Practice, Second Edition, Chapter 36, Saunders, 1999, pp. 817-844.
Loftsson et al., "Pharmaceutical Applications of Cyclodextrins. 1. Drug Solubilization and Stabilization". Journal of Pharmaceutical Sciences, vol. 85, No. 10, Oct. 1996, pp. 1017-1025.
Lombard et al., "Clinical Efficacy of Pimobendan Versus Benazepril for the Treatment of Acquired Atrioventricular Valvular Disease in Dogs". Journal of the American Animal Hospital Association, vol. 42, No. 4, Jul./Aug. 2006, pp. 249-261.
Lombard, Christophe W., "Therapy of Congestive Heart Failure in Dogs with Pimobendan". Proceedings of the 18th Annual Veterinary Medical Forum, American College of Veterinary International Medicine, Seattle, WA, 2000, pp. 107-109.
Lord et al., "Radiology: Role of Radiology in Diagnosis and Management of Thoracic Disease". Textbook of Canine and Feline Cardiology: Principles and Clinical Practice, Second Edition, Chapter 7, Saunders, 1999, pp. 111-117.
Luis-Fuentes, Virginia, "The effect of pimobendan in English Cocker Spaniels and Doberman dogs with heart failure and idiopathic dilated cardiomyopathy (DCM)". Ingelheimer Dialog, Boehringer Inglehim Vetmedica GmbH, Jun. 2000, Frankfort/Mainz, pp. 8-11.
Lyon et al., "Near-Infrared Spectral Imaging for Quality Assurance of Pharmaceutical Products: Analysis of Tablets to Assess Powder Blend Homogeneity". AAPS PharmSciTech, vol. 3, No. 3, Art. 17, Sep. 2002, pp. 1-15.
Malik et al., "Permethrin Spot-On Intoxication of Cats: Literature review and survey of veterinary practitioners in Australia". Journal of Feline Medicine and Surgery, vol. 12, 2010, pp. 5-14.
Mamoru et al., "Effects of Long-term, Very-low-dose Pimobendan for Patients with Diastolic Heart Failure". Journal of Cardial Failure, vol. 12, No. 8, Oct. 2006, p. S171.
Matsumori et al., "Pharmacology letters: Accelerated Communication: Pimobendan inhibits the activation of transcription factor NF-kB a mechanism which explains its inhibition of cytokine production and inducible nitric oxide synthase". Life Sciences, vol. 67, 2000, pp. 2513-2519.
McCrohon et al., "Differentiation of Heart Failure Related to Dilated Cardiomyopathy and Coronary Artery Disease Using Gadolinium-Enhanced Cardiovascular Magnetic Resonance". Circulation, vol. 108, Jul. 2003, pp. 54-59. Originally published online Jun. 23, 2003, http://circ.ahajournals.org, 7 pages.
Medline, homogeneous, Merriam-Webster, Last Accessed Feb. 10, 2011, 1 page, http://www.merriam-webster.com/medlineplus/homogeneous.
Menard et al., "Physico-Chemical Aspects of the Complexation of Some Drugs with Cyclodextrins". Drug Development and Industrial Pharmacy, vol. 16, No. 1, 1990, pp. 91-113.
Merriam-Webster, homogeneous, Last Accessed Feb. 10, 2011, 2 pages, http://www.merriam-webster.com/dictionary/homogeneous.
Monnet et al., "Idiopathic Dilated Cardiomyopathy in Dogs: Survival and Prognostic Indicators". 1995, Journal of Veterinary Internal Medicine, vol. 9, No. 1, pp. 12-17.
Ng, Tien M.H., "Levosimendan, a New Calcium-Sensitizing Inotrope for Heart Failure". Pharmacotherapy, vol. 24, No. 10, 2004, pp. 1366-1384.
O'Grady, et al., "Does Angiotensin Converting Enzyme Inhibitor Therapy Delay the Onset of Congestive Heart Failure or Sudden Death in Doberman Pinschers with Occult Dilated Cardiomyopathy?" Acvim Abstracts, 1997, p. 138.
Ohte et al., "The Cardia Effects of Pimobendan (But Not Amrinone) Are Preserved at Rest and During Exercise in Conscious Dogs with Pacing-Induced Heart Failure". The Journal of Pharmacology and Experimental Therapeutics, vol. 282, No. 1, 1997, pp. 23-31.
Okazaki et al., "A genetic linkage map of the Syrian hamster and localization of cariomyopathy locus on chromosome 9qa2.1-b1 using RLGS spot-mapping". Nature Genetics, vol. 13, May 1996, pp. 87-90.
Packer et al., "Effect of Oral Milrinone on Mortality in Severe Chronic Heart Failure." The New England Journal of Medicine, vol. 325, No. 21, Nov. 1991, pp. 1468-1475.
Pagel et al., "Influence of levosimendan, pimobendan, and milrinone on the regional distribution of cardiac output in anaesthetized dogs". British Journal of Pharmacology, vol. 119, 1996, pp. 609-615.
"905 Uniformity of Dosage Units". 2011 the United States Pharmacopeial Convention, Stage 6 Harmonization, Dec. 1, 2011, pp. 1-3.
"Cardiovascular system". MIMS, IVS Annual, Chapter 5, 2003, p. 104.
"Citric Acid". The Merck Index, An Encyclopedia of Chemicals, Drugs, and Biologicals, 13th Edition, Merck Research Laboratories Division of Merck & Co., Inc., Whitehouse Station, NJ, Index 2350, 2001, pp. 405-406.

(56) References Cited

OTHER PUBLICATIONS

"Guidance for Industry, Container Closure Systems for Packaging Human Drugs and Biologics: Chemistry, Manufacturing, and Controils Documentation". U.S. Department of Health and Human Services Food and Drug Administration, May 1999, pp. 1-56.
"Pharmaceutical Necessities". Remington's Pharmaceutical Sciences, 18th Edition, Mack Publishing Company, Easton, Pennsylvania, Chapter 66, 1990, pp. 1288-1300.
"Pimobendan". The Merck Index, An Encyclopedia of Chemicals, Drugs, and Biologicals, 13th Edition, Merck Research Laboratories Division of Merck & Co., Inc., Whitehouse Station, NJ, Index 7515, 2001, p. 1332.
Abstract in English for CN1702243A, 2005.
Abstract in English for DE3728244,1989.
Abstract in English for EP0306846, 1989.
Abstract in English for EP0330052, 1989.
Abstract in English for JP2005281283, 2005.
Abstract in English of JPH0570612, 1993.
Abstract in English of JPH11228302, 1999.
Ahmed et al., "Pharmaceutical challenges in veterinary product development". Advanced Drug Delivery Reviews, vol. 54, 2002, pp. 871-882.
Asanoi et al., "Disparate Inotropic and Lusitropic Responses to Pimobendan in Conscious Dogs with Tachycardia-Induced Heart Failure". Journal of Cardiovascular Pharmacology, vol. 23, No. 2, 1994, pp. 268-274.
Atkins et al., "Guidelines for the Diagnosis and Treatment of Canine Chronic Valvular Heart Disease". Journal of Veterinary Internal Medicine, vol. 23, No. 6, 2009, pp. 1-9.
Banker et al., "Uniformity of Dosage Units". Modern Pharmaceutics, Fourth Edition, Revised and Expanded, Marcel Dekker, Inc., New York, NY, 2006, p. 498.
Bassani et al., "Enhanced Water-Solubility of Albendazole by Hydroxy-Propyl-ß-Cyclodextrin Complexation". Journal of Inclusion Phenomena and Molecular Recognition in Chemistry, vol. 25, No. 1-3, Mar. 1996, pp. 149-152.
Bastien et al., "Chronic AT receptor blockade and angiotensin-converting enzyme (ACE) inhibition in (CHF 146) cardiomyopathic hamsters: effects on cardiac hypertrophy and survival". Cardiovascular Research, vol. 43, 1999, pp. 77-85.
Baur et al., "Cardiac remodelling and myocardial contractility in patients with congestive heart failure treated with furosemide and enalapril". Basic Research in Cardiology, vol. 86, Supp. 1, 1991, pp. 157-163.
Beers, et al., Merck Manual of Diagnosis and Therapy, 17th Edition, Chapter 203, Section 16, Merck Research Laboratories, Whitehouse Station, NJ, USA, 1999, pp. 1688-1692.
Berny et al., "Review: Animal Poisoning in Europe. Part 2: Companion Animals". The Veterinary Journal, vol. 193, 2010, pp. 255-259.
Boehringer Ingelheim Vetmedica GmbH, 1st International Canine Valvular Disease Symposium, Paris, Oct. 30-31, 2004, pp. 1-45.
Boehringer Ingelheim Vetmedica, Inc. "Freedom of Information Summary: Original New Animal Drug Application". NADA 141-273, Vetmedin, Pimobendan Chewable Tablets, Apr. 30, 2007, pp. 1-46.
Borgarelli et al., "Canine Idiopathic Dilated Cardiomyopathy. Part II: Pathophysiology and therapy". The Veterinary Journal, vol. 162, 2001, pp. 182-195.
Bozzone, Scott, "Solid Oral Dosage Forms Powder Blending" and "Solid Oral Dosage Forms, Blend Uniformity: Principles and Examples". Pfizer, IKEV Meeting, May 31, 2001, pp. 1-66.
Brewster et al., "Cyclodextrins as pharmaceutical solubilizers". Advanced Drug Delivery Reviews, vol. 59, No. 7, 2007, pp. 645-666.
Buchanan et al. "Vertebral scale system to measure canine heart size in radiographs". Journal of the American Veterinary Medical Association, vol. 206, No. 2, Jan. 1995, pp. 194-199.

Burlage et al., "Other Pharmaceutical Adjuncts"., Physical and Technical Pharmacy, The Blakiston Division: The McGraw-Hill Book Company, Inc., New York, 1963, pp. 653-662.
Calvert et al., "Congestive cardiomyopathy in Doberman Pinscher dogs". Journal of the American Veterinary Medical Association, vol. 181, 1982, pp. 598-602.
Calvert et al., "Signalment, Survival, and Prognostic Factors in Doberman Pinschers With End-Stage Cardiomyopathy". Journal of Veterinary Internal Medicine, vol. 11, No. 6, 1997, pp. 323-326.
Cambridge Dictionary, homogeneous, Last Accessed Feb. 10, 2011, 1 page, http://dictionary.cambridge.org/dictionary/british/homogeneous.
Chambers 21st Century Dictionary, homogeneous, Last Accessed Feb. 10, 2011, 1 page, http://www.xreferplus.com/entry/chambdict/homogeneous.
Chetboul, et al., "Comparitive Adverse Cardiac Effects of Pimobendan and Benazepril Monotherapy in Dogs with Mild Degenerative Mitral Valve Disease: A Prospective, Controlled, Blinded, and Randomized Study". Journal of Veterinary Internal Medicine, vol. 21, 2007, pp. 742-753.
Choy et al., "Scaling of myocardial mass to flow and morphometry of coronary arteries". Journal of Applied Physiology, vol. 104, 2008, pp. 1281-1286.
Cohn et al., "Cardiac Remodeling-Concepts and Clinical Implications: A Consensus Paper From an International Forum on Cardiac Remodeling". Journal of the American College of Cardiology, vol. 35, No. 3, 2000, pp. 569-582.
Collins English Dictionary, homogeneous, Last Accessed Feb. 10, 2011, 1 page, http://xreferplus.com/entry/hcengdict/homogeneous.
Conlon, P.D., "Nonsteroidal Drugs Used in the Treatment of Inflammation". Veterinary Clinics of North America: Small Animal Practice, vol. 18, No. 6, Nov. 1988, pp. 1115-1131.
Cowley et al, "Treatment of severe heart failure: quantity or quality of life? A trial of enoximone"., British Heart Journal, vol. 72, 1994, pp. 226-230.
Côté et al., "Congestive Heart Failure". Feline Cardiology, Ch. 19, Wiley-Blackwell, ISBN 978-0-8138-1242-7, 2011, p. 259.
Deneke et al., "Medikamentöse Therapie der Herzinsuffizienz". Herzschr Elektrophys, vol. 15, Suppl. 1, 2004, pp. 1/74-1/80.
Dictionary of Veterinary Drugs and Animal Health Products Marketed in France, 12th Edition, 2003, 3 pages.
El-Hagrasy et al., "A Process Analytical Technology Approach to Near-Infrared Process Control of Pharmaceutical Power Blending: Part II: Qualitative Near-Infrared Models for Prediction of Blend Homogeneity". Journal of Pharmaceutical Sciences, vol. 95, No. 2, Feb. 2006, pp. 407-421.
El-Hagrasy et al., "Near-Infrared Spectroscopy and Imaging for the Monitoring of Powder Blend Homogeneity". Journal of Pharmaceutical Sciences, vol. 90, No. 9, Sep. 2001,. pp. 1298-1307.
Elliott, P., "Diagnosis and management of dilated cardiomyopathy". Heart, vol. 83, 2000, pp. 106-112.
Endoh, Masao, "New Aspects of the Treatment of Myocardial Failure from a Pharmacological Standpoint". Journal of Clinical and Experimental Medicine, vol. 187, No. 10, 1998, pp. 827-831.
Erhardt, L., "An Emerging Role for Calcium Sensitisation in the Treatment of Heart Failure". Expert Opinion on Investigational Drugs, vol. 14, No. 6, 2005, pp. 659-670.
Ettinger et al., "Effects of enalapril maleate on survival of dogs with naturally acquired heart failure". Journal of the American Veterinary Medical Association, vol. 213, No. 11, 1998, pp. 1573-1577.
Fitton et al., "Pimobendan. A Review of its Pharmacology and Therapeutic Potential in Congestive Heart Failure". Drugs and Aging, vol. 4, No. 5, 1994, pp. 417-441.
Fox et al., "Prosepective Double-Blinded, Multicenter Evaluation of Chronic Therapies for Feline Diastolic Heart Failure: Interim Analysis". ACVIM Abstracts, Abstract 78, 2003, pp. 398-399.
Pagel et al., "Comparison of the effects of levosimendn, pimobendan, and milrinone on canine left ventricular-arterial coupling and mechanical efficiency", Basic Respiratory Cardiology, vol. 91, 1996, pp. 296-307.

(56) References Cited

OTHER PUBLICATIONS

Permanetter et al., "Acute Effects of Intraveneous UD-CG 115 BS (Pimobendan) on the Cardiovascular System and Left Ventricular Pump Function". Journal of Cardiovascular Pharmacology, vol. 14, Supp. 2, 1989, pp. S36-S40.
Phillips et al., "The challenge of gene therapy and DNA delivery". Journal of Pharmacy and Pharmacology, vol. 53, 2001, pp. 1169-1174.
Piel et al., "Development of a parenteral and of an oral formulation of albendazole with cyclodextrins". S.T.P. Pharma Sciences, vol. 9, No. 3, 1999, pp. 257-260.
Pirollo et al., "Targeted Delivery of Small Interfering RNA: Approaching Effective Cancer Therapies". Cancer Research, vol. 68, No. 5, Mar. 2008, pp. 1247-1250.
Rackley, Charles E., "Diseases of the Heart and Pericardium"., The Merck Manual, Chapter 25, 16th Edition, 1992, pp. 446-459.
Remme et al., "Hemodynamic Effects of Intravenous Pimobendan in Patients with Left Ventricular Dysfunction". Journal of Cardiovascular Pharmacology, vol. 15, Supp. 2, 1989, pp. S41-S44.
Remme et al., "Hemodynamic, Neurohumoral, and Myocardial Energetic Effects of Pimobendan, a Novel Calcium-Sensitizing Compound, in Patients with Mild to Moderate Heart Failure". Journal of Cardiovascular Pharmacology, vol. 24, No. 5, 1994, pp. 730-739.
Rinsyo to Kenkyu, "A case of diastolic hypertrophic cardiomyopathy in which sinus bradycardia and associated cardiac failure were improved as a result of cilostazol administration." The Japanese Journal of Clinical and Experimental Medicine, vol. 83, No. 5, May 2006, pp. 125-130.
Rodriguez, Damon B., "Treatment of Feline Hypertrophic Cardiomyopathy*". Compendium, vol. 24, No. 6, Jun. 2002, pp. 470-476.
Roland et al., "The Use of Pimobendan in Feline Heart Failure Secondary to Spontaneous Heart Disease". The 18th Annual ECVIM Congress, Abstract, Belgium, Sep. 2008, 1 page.
Rudnic et al., "Oral Solid Dosage Forms". Remington: The Science and Practice of Pharmacy, 20th Edition, Lippincott Williams & Wilkins, Baltimore, Maryland, Chapter 45, 2000, pp. 858-870.
Saavedra et al., "Reverse Remodeling and Enhanced Adrenergic Reserve From Passive External Support in Experimental Dilated Heart Failure". Journal of the American College of Cariology, vol. 39, No. 12, 2002, pp. 2069-1076.
Sabbah et al., "Effects of long-term monotherapy with enalapril, metoprolol, and digoxin on the progression of left ventricular dysfuntion and dilation in dogs with reduced ejection fraction". Circulation, vol. 89, 1994, pp. 2852-2859.
Sabbah, Hani N., "The Cardiac Support Device and the Myosplint: Treating Heart Failure by Targeting Left Ventricular Size and Shape". The Annals of Thoracic Surgery, vol. 75, 2003, pp. S13-S19.
Shiga et al., "b-Blocker Therapy Combined with Low-Dose Pimobendan in Patients with Idiopathic Dilated Cardiomyopathy and Chronic Obstructive Pulmonary Disease: Report on Two Cases". Cardiovascular Drugs and Therapy, vol. 16, 2002, pp. 259-263.
Sisson et al., "Myocardial Diseases of Dogs". Textbook of Canine and Feline Cardiology: Principles and Clinical Practice, Second Edition, Chapter 27, Saunders, 1999, pp. 581-619.
Sisson, David, "Lecture Notes: Cardiology", The District of Columbia Academy of Veterinary Medicine, May 2001, pp. 1-18.
Summerfield et al., "Efficacy of Pimobendan in the Prevention of Congestive Heart Failure or Sudden Death in Doberman Pinschers with Preclinical Dilated Cardiomyopathy (The PROTECT Study)". Journal of Veterinary Internal Medicine, vol. 26, 2012, pp. 1337-1349.
Takeda et al., "Normalization of Left Ventricular Parameters Following Combined Pimobendan and Carvedilol Treatment in a Case of Unclassified Cardiomyopathy with Longstanding Refractory Status". Internal Medicine, vol. 41, No. 12, Dec. 2002, pp. 1147-1152.
The American Heritage Dictionary, homogeneous, Last Accessed Feb. 10, 2011, 1 page, http://www.xreferplus.com/entry/hmdictenglang/homogeneous.
Tomanek et al., "Growth of the Coronary Vasculature in Hypertrophy: Mechanisms and Model Dependence". Cellular and Molecular Biology Research, vol. 40, No. 2, 1994, pp. 129-136.
Van Meel et al., "Pimobendan Increases Survival of Cardiomyopathic Hamsters". Journal of Cardiovascular Pharmacology, vol. 13, 1989, pp. 508-509.
Vidal et al., "Making sense of antisense". European Journal of Cancer, vol. 41, 2005, pp. 2812-2818.
Villar et al., "Ibuprofen, Aspirin and Acetaminophen Toxicosis and Treatment in Dogs and Cats". Veterinary and Human Toxicology, vol. 40, No. 3, Jun. 1998, pp. 156-162.
Wikipedia, the Free Encyclopedia, "Milrinone". [Accessed at: http://en.wikipedia.org/wiki/Milrinone on Mar. 10, 2014].
Wikipedia, the Free Encyclopedia, "Pimobendan". [Accessed at: http://en.wikipedia.org/wiki/Pimobenan on Mar. 10, 2014].
Woolley et al., "Effects of Treatment Type on Vertebral Heart Size in Dogs With Myxomatous Mitral Valve Disease". The Journal of Applied Research in Veterinary Medicine, vol. 5, No. 1, 2007, pp. 43-48.
Ettinger et al., "Therapeutic Considerations in Medicine and Disease". Textbook of Veterinary Internal Medicine, Diseases of the Dog and Cat, Sixth Edition, vol. I, 2004, pp. 530-531.
Stuber et al., "The Pharmaceutical and Biological Availability of Commercial Preparations of Furosemide". Arzneimittel-Forschung, vol. 32, No. 6, 1982, pp. 693-697.
Kitzen et al., "Pimobendan". Cardiovascular Drug Reviews, vol. 6, No. 4, 1989, pp. 265-291.
Lezcano et al., "Complexation of Several Benzimidazole-Type Fungicides with Alpha and Beta-Cyclodextrins". Journal of Agricultural and Food Chemistry, vol. 50, 2002, pp. 108-112.
Redenti et al., "Drug/Cyclodextrin/Hydroxy Acid Multicomponent Systems. Properties and Pharmaceutical Applications". Journal of Pharmaceutical Sciences, vol. 89, 2000, pp. 1-8.
Fraker et al., "Reversal of phosphate induced decreases in force by the benzimidazole pyridazinone, UD-CG 212 CL, in myofilaments from human ventricle." Molecular and Cellular Biochemistry, vol. 176, 1997, pp. 83-88.
Kanno, et al., "Effects of Pimobendan for Mitral Valve Regurgitation in Dogs", Laboratories of Veterinary Internal Medicine and Veterinary Pathobiology, pp. 373-377.
Bourezg, et al., "Redispersible lipid nanoparticles of Spironolactone obtained by three drying methods", Colloids and Surfaces A: Physicochemical and Engineering Aspects, 413 (2012), pp. 191-199.
El-Badry et al., "Physicochemical Characterization and Dissolution Properties of Meloxicam-Gelucire 50/13 Binary Systems." Scientia Pharmaceutica, vol. 79, 2011, pp. 375-386.
Fasinu, et al., "Diverse approaches for the enhancement of oral drug bioavailability", Biopharmaceutics & Drug Disposition, 32: pp. 185-209, 2011.
Beaufrere, et al., Therapeutic Review, "Pimobendan", Journal of Exotic Pet Medicine, vol. 18, No. 4, Oct. 2009, pp. 311-313.
Boswood et al., "Evaluation of pimobendan in dogs with cardiomegaly caused by preclinical mitral valve disease." The Veterinary Record, vol. 168, No. 8, Feb. 2011, p. 222.
Boswood et al., "Effect of Pimobendan in Dogs with Preclinical Myxomatous Mitral Valve Disease and cardiomegaly: the EPIC Study—A Randomized Clinical Trial." Journal of Veterinary Internal Medicine, vol. 30, 2016, pp. 1765-1779.
Atkins, et al. "Pharmacologic management of myxiomatous mitral valve disease in dogs", Journal of Veterinary Cardiology (2012), 14, pp. 165-184.
Ouellet, et al., "Effect of Pimobendan on Echocardiographic Values in Dogs with Asymptomatic Mitral Valve Disease", Journal of Veterinary Med., 2009; 23: pp. 258-263.
Upadhyay, et al., "Formulation of Fast-Release Gastroretentive Solid Dispersion of Glibenclamide with Gelucire 50/13", Tropical Journal of Pharmaceutical Research, Jun. 2012: 11 (3), pp. 361-369.

(56) References Cited

OTHER PUBLICATIONS

Vasconcelos, et al., "Sold dispersions as strategy to improve oral bioavailability of poor water soluble drugs", Drug Discovery Today, vol. 12, Nos. 23/24, Dec. 2007, pp. 1068-1075.
Lindenberg, et al., "Classification of orally administered drugs on the World Health Organization Model list of Essential Medicines according to the biopharmaceutics classification system", European Journal of Pharmaceutics and Biopharmaceutics 58 (2004), pp. 265-278.
Nainar, et al., "Biopharmaceutical Classification system in In-vitro/In-vivo Correlation: Concept and Development Strategies in Drug Delivery", Tropical Journal of Pharmaceutical Research, Apr. 2012; 11 (2), pp. 319-329.
Liu et al., "Pharmacology Preparation Technology." Chemical Industry Press, 2006, pp. 113-114.
Sun et al., "Pimobendan." Chemical Industry Press, 2002, pp. 29-30.
C. Atkins et al. "Guidelines for the Diagnosis and Treatment of Canine Chronic Valvular Heart Disease," J. Vet. Intern. Med. 2009; 23: 1142-1150. 2009.
E. Madron et al. "Survival and echocardiographic data in dogs with congestive heart failure caused by mitral valve disease and treated by multiple drugs: A retrospective study of 21 cases," Can. Vet. J. Nov. 2011, 52(11) 1219-1225.
English translation of Foreign Patent Document No. 8, JP2005-281283A, of the current Information Disclosure Statement, Oct. 2005.
Lombard, C., "Clinical efficacy of pimobendan in double-blind clinical trial," at http://www.vetcontact.com/en/print.php?a=417, published Jul. 21, 2004, accessed on Feb. 18, 2016.
O'Grady M.R. et al. "Effect of Pimobendan on Case Fatality Rate in Doberman Pinschers with Congestive Heart Failure Caused by Dilated Cardiomyopathy," J. Vet. Intern. Med. 2008; 22: 897-904.
Divya .A et al., "Bilayer tablet technology: An overview," Journal of Applied Pharmaceutical Science 01 (08); 2011: 43-47.
Deshpande et al., "Bi-Layer Tablets—An Emerging Trend: A Review," IJPSR, 2011; vol. 2(10): 2534-2544.
Document "Lotensin (benazepril hydrochloride) Tablet" NDA Approved Feb. 2, 2007, pp. 1-18, US Food and Drug Administration, accessed at https://docslide.net/documents/lotensin-benazepril-hydrochloride-tablet-t2006-83-lotensin-.html on Jul. 13, 2018.
Freedom of Information Summary Original New Animal Drug Application NADA 141-273 Vetmedin Pimobendan Chewable Tablets, Apr. 7, 2007.
Rompp Chemie Lexikon, 9th Ed., 1999, Georg Thieme Verlag Stuttgart New York, p. 1641.
Document D17 cited in Opposition to EP 2793866, published Jan. 30, 2017, in the EP Patent Register for EP Application No. 12813324.
European Pharmacopeia, 7th Ed., 2010, European Pharmacopeia Commission, p. 1454.
M. Gana et al. "Kinetics of the acidic and enzymatic hydrolysis of benazepril HCI studied by LC," Journal of Pharmaceutical and Biomedical Analysis 27 (2002) pp. 107-116.
Wikipedia entry "Amlopidine", https://en.wikipedia.org/wiki/Amlopidine, accessed Jun. 2, 2017.
Document D25, Declaration of Dr. Martin Folger, cited in Opposition to EP 2793866, published Aug. 3, 2017, in the EP Patent Register for EP Application No. 12813324.
Document D26, Curriculum Vitae of Dr. Martin Folger, cited in Opposition to EP 2793866, published Aug. 3, 2017, in the EP Patent Register for EP Application No. 12813324.
Document D27, Publication List of Dr. Martin Folger, cited in Opposition to EP 2793866, published Aug. 3, 2017, in the EP Patent Register for EP Application No. 12813324.
Document D28, Declaration of Dr. Mateja Sikovec, cited in Opposition to EP 2793866, published Oct. 12, 2017, in the EP Patent Register for EP Application No. 12813324.
Document D29, Test Data of Dr. Mateja Sikovec, cited in Opposition to EP 2793866, published Oct. 12, 2017, in the EP Patent Register for EP Application No. 12813324.
Document D30, Declaration of Dr. Stefan Haas, cited in Opposition to EP 2793866, published Oct. 12, 2017, in the EP Patent Register for EP Application No. 12813324.
Salsa, T. et al., "Oral Controlled-Release Dosage Forms. I. Cellulose Ether Polymers in Hydrophilic Matrices," Drug Development and Industrial Pharmacy, 23(9) pp. 929-938 (1997).
Lachman, L. et al. "The Theory and Practice of Industrial Pharmacy," Lea & Febiger, Philadelphia, 1965, p. 330 and p. 221.
Voigt, R., et al. "Lehrbuch der pharmazeutischen Technologie," Ver Verlag Volk und Gesundheit, Berlin, 1973, pp. 131, 132, 158, 159, 228, 229.
Parikh, D. ed., "Handbook of Pharmaceutical Granulation Technology," Marcel Decker, New York, NY, 1997, pp. 5-23.
Serno, P. et al. Granulieren Grundlagen, Verfahren, Formulierungen 2. ueberarbeitete und erweiterte Auflage, Editio Cantor Verlag Aulendorf Germany (2016) pp. 11-38.

\* cited by examiner

PHARMACEUTICAL TABLET FORMULATION FOR THE VETERINARY MEDICAL SECTOR, METHOD OF PRODUCTION AND USE THEREOF

FIELD OF THE INVENTION

The present invention is directed to a pharmaceutical tablet formulation for the veterinary medical sector. Particularly, the present invention relates to a pharmaceutical tablet formulation for the veterinary medical sector containing two pharmaceutically active substances at the same time. The present invention also discloses an intermediate product, namely the granules contained in the pharmaceutical tablet formulation of the present invention, a method of production of the pharmaceutical tablet formulation, a method of production of the granules and the use thereof.

BACKGROUND OF THE INVENTION

In contrast to medicaments for humans, in the case of animal medicine the arising problems are completely different. A dosage in a form which is, for example, appropriate for oral consumption which has been tailored for human patients is not per se suitable for the administration to an animal. If, for example, a pharmaceutical active ingredient has a taste which is unpleasant to the animal, the animal will refuse to take it orally.

Furthermore, when the animals concerned are domestic animals, the animal keeper always prefers to use an easy and time-saving therapy to treat the animals. In addition simple and safe application forms are required, which, after diagnosis and indication by the veterinarian, can be given by the animal keeper himself/herself. Therefore, dosage forms are required which are eaten willingly and without problems by the animals, components which are found to be unpleasant or repulsive by the animal's sense of taste and smell should be avoided. In addition, an application form is required which allows the animal owner to control whether the administered dose has been taken up completely. This is e.g. achieved by offering a tablet which is voluntarily taken by the animal. Furthermore, in the particular situation the drug product is not administered by the patient (which is the diseased animal), but by the animal owner. Since any kind of interference will be stressful for the animal and as a result for the animal owner, the possibility of applying a free-choice medication will not only ensure convenience for the animal owner—especially for a drug product for the treatment of a chronic disease which has to be given over months once or twice a day—but will also support compliance by guaranteeing that the prescribed dose will be given and the treatment not terminated due to lack of acceptance.

Sometimes there are also stability problems with the active ingredient or ingredients contained in the medicaments which would result in an unavoidable loss of active ingredient(s), whereby the treatment effectivity and control of the therapy would be significantly violated.

Taking the above items into account, it is a basic aim of the present invention to develop a pharmaceutical combination form of the active substance pimobendan and an ACE inhibitor, both known in therapy to treat heart diseases in animals, and to provide an application form which is suitable for animal medicine, which can be used in a controlled manner without considerable effort and in a comfortable manner, such as on a daily basis, particularly for domestic animals, in the case of pets such as dogs and cats.

The characteristics and mode of action of the active substance pimobendan as well as the substance group of ACE inhibitors are known:

Pimobendan is the chemical substance (RS)-6-[2-(4-methoxyphenyl)-1H-benzimidazol-5-yl]-5-methyl-4,5-dihydropyridazin-3(2H)-one and has the following chemical formula:

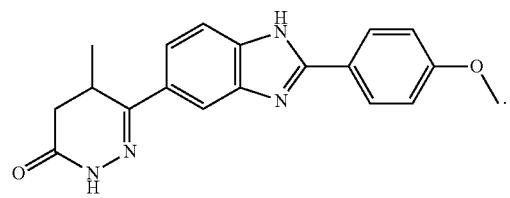 [SMILES: COc1ccc(-c2nc3cc(C4=NNC(=O)CC4C)ccc3[nH]2)cc1]

It is a known cardiotonic vasodilator (inodilator) which derives its inotropic activity from a combination of phosphodiesterase III inhibition and sensitisation of myocardial contractile proteins to calcium. It is a chemically stable substance having a poor and pH-dependent solubility, it is better soluble in acid. The resorption, when administered orally, is prone to considerable inter- and intra-individual fluctuations if the active substance is incorporated in conventional pharmaceutical forms for oral administration. In solid medicaments pimobendan is often mixed with citric acid in order to improve the solubility and dissolution, and to maintain a potentially oversaturated solution as long as possible.

An ACE inhibitor is an angiotensin converting enzyme inhibitor which lowers blood pressure by inhibiting the formation of angiotensin II, thus relaxing the arteries, and consequently improves the pumping efficiency and cardiac output. ACE inhibitors are generally very difficult to formulate into dosage forms, as most ACE inhibitors on contact with some of the commonly used pharmaceutical ingredients undergo degradation at accelerated rates due to cyclization via internal nucleophilic attack to form substituted diketopiperazines or hydrolysis of the side chain ester group. For example, benazepril is a known ACE inhibitor. Benazepril is the chemical substance [S—(R*,R*J]-3-[[1-(ethoxycarbonyl)-3-phenylpropyl]amino]-2,3,4,5-tetrahydro-2-oxo-1H-1-benzazepin-1-acetic acid and has the following chemical formula:

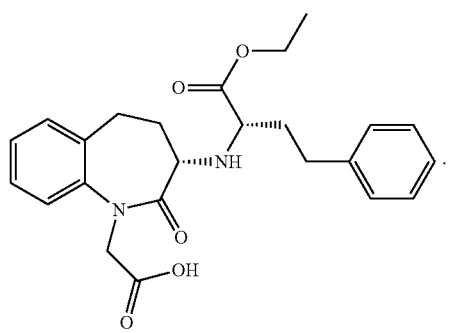 [SMILES: CCOC(=O)[C@H](CCc1ccccc1)N[C@H]1CCc2ccccc2N(CC(=O)O)C1=O]

It is a moisture and pH sensitive, well water-soluble and bitter tasting substance. In case of humidity a hydrolysis of benazepril or a pharmaceutically acceptable salt thereof is to be expected. Due to the very bitter taste it is difficult to formulate conventional palatable dosage forms.

The above substance-related particularities make it difficult to develop a pharmaceutical formulation wherein both active substances are present whereby a good long-term stability, the required release properties, and taste masking are provided.

In prior art a number of pharmaceutical formulations are described which contain an ACE inhibitor such as benazepril or a pharmaceutically acceptable salt thereof:

EP 1 490 037 B1 describes an animal medicine consisting of a substrate in pellet or tablet form, which is attractive to livestock and domestic animals and which consists of dry feed for animals on a vegetable and/or animal basis, in which fine-grained particles of a neutral-tasting, physiologically compatible, solid carrier material are embedded, whereby said fine-grained particles of carrier material have an average diameter of 0.09 to 0.8 mm and are coated with benazepril, and said benazepril layer is encased with a protective layer of a physiologically compatible polymer matrix. The physiologically compatible polymer matrix is selected from the group consisting of: shellac, a polymer on a cellulose, acrylic acid or methacrylic acid, maleic acid anhydride, polyvinyl pyrrolidone and polyvinyl alcohol basis. Also the production and usage of a preparation for veterinary medicine is disclosed.

EP 1 385 489 B1 is directed to granules based on angiotensin converting enzyme inhibitor, its isomers or its pharmaceutically acceptable salts, whereby they are coated and contain ACE inhibitor monocrystals, one or several binding agents selected from the group comprising in particular cellulosic polymers, in particular ethyl cellulose, hydroxypropyl cellulose, and hydroxypropyl methyl cellulose, acrylic polymers, polyvidones, polyvinyl alcohols, and mixtures thereof, optionally a diluent selected from the group consisting in particular of cellulosic derivatives, starches, lactose and polyols, in particular mannitol, and an anti-static agent selected from the group comprising in particular colloidal silica, precipitated silica and micronized or non-micronized talcum. Benazepril is mentioned as an example of an ACE inhibitor. It is also described the method for preparing said granules and rapidly disintegrating tablets based on the coated granules, which disaggregate in the mouth on contact with salvia in less than 60 seconds.

However, a pharmaceutical formulation containing an ACE inhibitor or a pharmaceutically acceptable salt thereof as well as pimobendan or a pharmaceutically acceptable salt thereof is not known up to now.

It is therefore an object of the present invention to provide an improved pharmaceutical formulation which avoids the disadvantages of the prior art and wherein an ACE inhibitor or a pharmaceutically acceptable salt thereof and pimobendan or a pharmaceutically acceptable salt thereof are present at the same time. The formulation shall allow to mask the bitter taste of the ACE inhibitor or a pharmaceutically acceptable salt thereof whereby the stability thereof shall be assured and the release of pimobendan or a pharmaceutically acceptable salt thereof shall not be hindered in any way. Preferably the combined formulation of both active substances shall be bioequivalent to the respective monoproducts. The choice of the excipients and/or additives contained in the formulation shall support and improve the stability of an ACE inhibitor or a pharmaceutically acceptable salt thereof present. Furthermore, the formulation shall not lead to particular inacceptance problems when administerd to animals, but should allow free uptake by the animal during chronic treatment over the whole administration period with equal or better acceptance compared to the existing individual tablet formulations containing either pimobendan or an ACE inhibitor as active pharmaceutical ingredient. In addition, a method of manufacturing the formulation shall be provided.

DESCRIPTION OF THE INVENTION

Surprisingly, it has been found that a pharmaceutical tablet formulation for the veterinary medical sector is provided, which contains an instable ACE-inhibitor or acceptable salt thereof as well as a PDE-inhibitor or a pharmaceutically acceptable salt thereof, which needs to be in the vicinity of acid in order to achieve bioavailability. It is therefore provided a pharmaceutical tablet formulation for the veterinary medical sector containing an acid-instable ACE-inhibitor or a pharmaceutically acceptable salt thereof as a first pharmaceutically active substance, and pimobendan or a pharmaceutically acceptable salt thereof as a second pharmaceutically active substance, comprising granules, which contain carrier core particles coated with at least one layer wherein the first pharmaceutically active substance is present, the granules being embedded in a tablet matrix wherein the second pharmaceutically active substance is present.

Instable ACE-inhibitors are herein defined to be ACE inhibitors, which easily undergo degradation when in contact with for example water, acids, flavours, lubricants or any other tabletting excipient, but especially ACE-inhibitors that are degraded by for example hydrolysis following contact with water, acids or flavour. Said ACE-inhibitors comprise or consist of benazepril, captopril, enalapril, lisinopril, quinapril, fosinopril, perindopril, imidapril, zofenopril, trandolapril and ramipril, preferred is benazepril.

According to a preferred embodiment of the present invention it has been found that a pharmaceutical tablet formulation for the veterinary medical sector is provided, which contains benazepril or a pharmaceutically acceptable salt thereof as well as pimobendan or a pharmaceutically acceptable salt thereof. It is therefore provided a pharmaceutical tablet formulation for the veterinary medical sector containing benazepril or a pharmaceutically acceptable salt thereof as a first pharmaceutically active substance, and pimobendan or a pharmaceutically acceptable salt thereof as a second pharmaceutically active substance, comprising granules, which contain carrier core particles coated with at least one layer wherein the first pharmaceutically active substance is present, the granules being embedded in a tablet matrix wherein the second pharmaceutically active substance is present.

The technical realisation is based on embedding the potentially instable ACE-inhibitor or a pharmaceutically acceptable salt thereof, preferably benazepril or a pharmaceutically acceptable salt thereof, containing granules in a tablet matrix wherein pimobendan or a pharmaceutically acceptable salt thereof is present. It has been found that the fixed dose combination of both active substances of the present invention provides a synergistic combination which exceeds the activity and effectivity of the single active substances.

The granules according to the present invention are not particularly limited. According to the frame of the present invention "granules" are associated aggregates of powder particles having a non-uniform surface and an inner structure. The aggregation results in a decrease of the specific surface area which leads to a reduced adhesion among the primary granule particles. Granules are in general more uniform than powders and allow a more homogeneous tablet mass and higher dosage accuracy to be achieved.

The inner structure of the granules according to the present invention is represented by the carrier core particles. The carrier core particles of the granules are preferably selected from a pharmaceutically acceptable material which upon contact with water shows a minimal or negligible swelling. Preferable materials are selected from lactose, carbohydrates, sugar alcohols, such as mannitol, sorbitol, maltitol, glucose, non-pareil-seeds, calcium phosphate, cellulose, preferably microcrystalline cellulose (MCC), and starch, and mixtures thereof, more preferably lactose, most preferably agglomerated α-lactose-monohydrate [Ph.Eur./USP-NF/JP] with a particle size $d_{50}$ of ca. 180 μm Lactose such as agglomerated lactose, with the characteristics described above is particularly suitable for use in the core because of its particle size, non-hygroscopicity, and the fact that it at least partly undergoes plastic deformation upon compression so that the core will not break into pieces in the tablet press. Particularly preferred are also mixtures of agglomerated α-lactose-monohydrate together with one or more of the other materials listed above.

According to a preferred embodiment of the present invention the carrier core particles are coated with a layer containing the instable ACE-inhibitor, preferably benazepril or a pharmaceutically acceptable salt thereof as the first pharmaceutically active substance, and a coating polymer and/or matrix forming polymer(s), optionally mixtures thereof.

Pharmaceutically acceptable salts of the instable ACE-inhibitor, preferably benazepril, include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfonic, tartaric, acetic, methanesulfonic, formic, benzoic, malonic, naphthalene-2-sulfuric and benzenesulfonic acids. The preferred pharmaceutically acceptable salt of benazepril is the hydrochloride.

The coating polymer and/or matrix forming polymers are for example water-soluble polymers such as cellulose ethers or pH-dependently soluble, or swellable polymers such as polymethacrylates, optionally in combination with pore forming agents, or water-insoluble polymers such as polymethacrylates or cellulose ethers in combination with pore forming agents. Water-soluble cellulose ethers are for example hydroxypropyl methylcellulose (HPMC), methylcellulose, hydroxyethylcellulose. Pore forming agents are for example water soluble cellulose ethers, polyethylene glycols, sugars and sugar alcohols like saccharose, lactose.

Preferred is a polymer on methacrylic acid basis which is a polymer from the group of polymethacrylates such as methaycrylic acid-ethyl acrylate copolymer (1:1).

Polymethacrylates are for example synthetic neutral/uncharged, or cationic and anionic polymers of monomers comprising dimethylaminoethyl methacrylates, methacrylic acid, and methacrylic acid esters in varying ratios. A polymethacrylate polymer which is soluble under acidic conditions, but insoluble under neutral or basic conditions is even more preferred. The mentioned polymer may be used alone or in combination of two or more polymers. According to a preferred embodiment of the present invention only one polymer is used.

Particularly preferred is a cationic copolymer based on dimethylaminoethyl methacrylate copolymer (IUPAC name: poly(butyl methacrylate-co-(2-dimethyl-aminoethyl) methacrylate-co-methyl methacrylate) 1:2:1) (also known as Basic Butylated Methacrylate Copolymer Ph. Eur). A number of compounds are commercially available products from the company Röhm, Darmstadt, Germany, which are known as substances belonging to the Eudragit® series. For example, a polymer on methacrylic acid basis, such as poly(butyl methacrylate-co-(2-dimethyl-aminoethyl) methacrylate-co-methyl methacrylate) 1:2:1 is a functional polymer, which is soluble in acidic medium, for example in gastric fluid up to pH 5, swellable and permeable above pH 5.0, but insoluble under neutral and basic conditions.

A coating polymer and/or matrix forming polymer(s), preferably a polymethacrylate polymer, which is soluble under acidic conditions, but insoluble under neutral or basic conditions—a particularly preferred polymer in the present invention—has the advantage that after administration of the pharmaceutical tablet formulation the polymer is not immediately dissolved in the mouth of the animal so that the first active substance, the instable ACE-inhibitor, preferably benazepril or a pharmaceutically acceptable salt thereof, is not released. Even in case one or more acidic excipients are present in the outer tablet phase, the acidic microclimate formed would not be sufficient to contribute to the dissolution of the polymer(s) and subsequently the first pharmaceutically active substance. The intake of the tablet is so rapid that such effects will play no part. Thus there will be no contact between the active substance and water avoiding immediate dissolution of the drug in the animal's mouth or possible hydrolysis at this stage of ingestion. Furthermore, as there is no dissolution of the tablet at this stage, any flavours or tastes that are unpleasant for the patient are masked. However, as soon as the pharmaceutical tablet formulation arrives in the stomach, the polymer is dissolved and the first active substance is rapidly and completely released. Thus, the formation of a bitter taste in the mouth of the animal due to the realease of the instable ACE-inhibitor, preferably benazepril or a pharmaceutically acceptable salt thereof is completely avoided.

According to a preferred embodiment of the present invention the coated carrier core particles are additionally coated with a layer containing at least a coating polymer and/or matrix forming polymer, preferably a polymer on methacrylic acid basis. The polymer on methacrylic acid basis is again a polymer which belongs to the polymethacrylates as already discussed. More preferably the polymer on methacrylic acid basis is a cationic copolymer based on dimethylaminoethyl methacrylate copolymer (IUPAC name: poly(butyl methacrylate-co-(2-dimethyl-aminoethyl) methacrylate-co-methyl methacrylate) 1:2:1, also known as Basic Butylated Methacrylate Copolymer Ph. Eur.

Therefore, the carrier core particles are coated with a layer containing the first pharmaceutically active substance and at least one coating polymer and/or matrix forming polymer, preferably a polymer on methacrylic acid basis. This layer is also referred herein as first or inner layer.

More preferably the coated carrier core particles are additionally coated with a layer containing at least one coating polymer and/or matrix forming polymer, preferably a polymer on methacrylic acid basis but no pharmaceutically active substance. This layer is herein referred to as second or outer layer.

The coating polymer and/or matrix forming polymer, preferably the polymethacrylate polymer(s), in the first coating layer is the same or different from the coating polymer and/or matrix forming polymer, preferably polymethacrylate polymer(s), used in the second coating layer. According to a particularly preferred embodiment the coating polymer and/or matrix forming polymer, preferably polymer(s) on methacrylic acid basis, in the two layers is (are) the same. In a further preferred embodiment of the present invention only one polymer on methacrylic basis is present in the first and the second layer and the polymer is the same in both layers, while other polymers can be present in either or both layer(s).

The coating polymer and/or matrix forming polymer, preferably a polymer on methacrylic acid basis present in the pharmaceutical tablet formulation of the present invention has several functions at the same time:

It serves to mask the bitter taste of the instable ACE-inhibitors, preferably benazepril or a pharmaceutically acceptable salt thereof because the bitter tasting first pharmaceutically active substance is embedded in the polymer. Furthermore, it provides stability to the resultant formulation. The polymer provides protection from surrounding moisture, as well as physical separation from additional excipients such as acids or flavouring agents that contribute to the instability of the ACE-inhibitor, preferably benazepril or a pharmaceutically acceptable salt thereof. In addition the release performance is optimized because the first active substance is not released immediately in the mouth of the animal as already described. Finally, the polymer binds the first pharmaceutically active substance to the carrier particles aiding homogeneous distribution of the active ingredient in the tablet, and further enhancing mechanical stability of the whole pharmaceutical tablet formulation. The resulting particles could also be administered as stand-alone granules for the ACE inhibitor or any salt thereof or be compressed with suitable excipients to a mono tablet thus underlining the flexibility and versatility of the particles as described above. The granules containing ACE inhibitor are well suited to be administered as granules or processed further into capsules or tablets. It has been observed that the shape and size of the granules according to the present invention provide an excellent mouth feeling so that animals willingly accept the intake of such granules as medicament. The granules may also form part of a combined preparation wherein the further dosage form comprises another pharmaceutically active substance.

As a result, the first layer is an important feature of the tablet formulation whereas the second layer further improves the above mentioned functions. According to another embodiment of the invention the second layer is optional.

It is a matter of course that one or more additional intermediate layers between the carrier core particles and the first layer and/or between the first and the second layer and/or between the second layer and the tablet matrix can optionally be present. Therefore, in another embodiment of the present invention the pharmaceutical tablet formulation comprises the above described carrier core particles coated with the first layer, the second layer and the tablet matrix and optionally one or more intermediate layers may be disposed between. The amount/number of intermediate layers are not limited. Any optional layer which does not interfere with the function and effectiveness of the pharmaceutical tablet formulation may be used such as a non-functional layer. The term "non-functional" in the present context means having no substantial effect on release properties of the pharmaceutical tablet formulation, and the layer in the form of a coating serves another useful purpose. For example, such a layer can impart a distinctive appearance to the dosage form, provide protection against attrition during packaging and transportation, improve ease of swallowing, and/or have other benefits. A layer or coating should be applied in an amount sufficient to provide complete coverage of the surface of the coated particles/granules.

In one embodiment according to the present invention the pharmaceutical tablet formulation comprises or consists of the carrier core particles coated with the first layer and the second layer and the tablet matrix. In this embodiment no intermediate layer is present.

In another embodiment according to the present invention the pharmaceutical tablet formulation comprises or consists of the carrier core particles coated with the first layer and the second layer and the tablet matrix, whereby one intermediate layer is present at one or more appropriate locations in the coated particles/granules.

The pharmaceutical tablet formulation according to the present invention comprises one or more excipients used according to pharmaceutical practice. Due to the different functionality the one or more polymer layer(s) on the coated particles as described above and the tablet matrix have a different composition with regard to the excipients present. As a result, the polymer layer(s) on the coated particles, for example the first and second layers, comprise one or more excipients, whereby the excipients are preferably selected from release modifying agents, binders, carriers, crystallization retarders, sweeteners, solubilizers, coloring agents, flavouring substances, pH control agents, taste masking agents, surfactants, anti-tacking agents, plasticizers, anti-static agents, and emulsifiers.

Furthermore, the tablet matrix comprises one or more excipients, whereby the excipients are preferably selected from binders, carriers, diluents, disintegrants, fillers, lubricants, acidifying agents, glidants, crystallization retarders, sweeteners, solubilizers, coloring agents, flavouring substances, pH control agents, taste masking agents, anti-tacking agents, plasticizers, surfactants, and emulsifiers.

The term "one or more" or "at least one" as used in the present invention stands for 1, 2, 3, 4, 5, 6, 7, 8, 9, 10 compounds or layers or even more. Some preferred embodiments comprise 1, 2, 3, 4, or 5 such compounds or layers. Some preferred embodiments comprise 1, 2, or 3 such compounds or layers, 1 or 2 compounds or layers or one compound or layer may also be employed.

Commonly known excipients used in the pharmaceutical tablet formulation of the present invention are listed in the following:

As binder, it is possible to use any binder usually employed in pharmaceuticals. Exemplarily mentioned are naturally occuring or partially or totally synthetic polymers selected from among acacia, agar, gum arabic, alginic acid, carbomers, carrageenan, ceratonia, chitosan, confectionar's sugar, copovidone, povidone, cottonseed oil, dextrate, dextrin, dextrose, polydextrose, maltodextrin, maltose, cellulose, and derivatives thereof such as microcrystalline cellulose, methylcelluloses, ethylcelluloses, hydroxyethyl celluloses, hydroxyethyl methylcelluloses, hydroxypropyl celluloses, carboxymethylcelluloses, carmellose sodium, hypromelloses (cellulose hydroxypropyl methylether), cellulose acetate phthalate, starch and derivatives thereof, such as pregelatinized starch, hydroxypropylstarch, corn starch, gelatin, glyceryl behenate, guar gum, hydrogenated vegetable oils, inulin, lactose, glucose, magnesium aluminium silicate, poloxamer, polycarbophils, polyethylene oxide, polyvinyl pyrrolidone, copolymers of N-vinylpyrrolidone and vinyl acetate, polymethacrylates, alginates auch as sodium alginate, stearic acid, sucrose, sunflower oil, zein as well as derivatives and mixtures thereof. Particularly preferred binders are gum arabic, hydroxypropyl celluloses, hydroxypropyl methylcelluloses, methylcelluloses, hydroxyethyl celluloses, carboxymethylcelluloses, carmellose sodium, povidone, corn starch, polyvinyl pyrrolidone, the copolymers of N-vinylpyrrolidone, and vinyl acetate, or combinations of these polymers.

Suitable carriers, diluents or fillers which are usually employed in pharmaceuticals may be selected from, for example, lactose, in particular lactose monohydrate, talc, sunflower oil, tragacanth, starches and derivatives such as pregelatinized starch or sterilizable maize, alginate such as ammonium alginate, sodium alginate, sodium chloride, calcium carbonate, dibasic calcium phosphate, calcium hydrogenophosphate, calcium sulfate, dicalcium or tricalcium phosphate, magnesium carbonate, magnesium oxide, cellulose and derivatives, such as microcrystalline or silicified or silicified microcrystalline cellulose, cellulose acetate, starch glycolate, ethylcellulose, sugars and derivatives such as confectioner's sugar, fructose, sucrose, dextrate, dextrin, sulfobutylether ß-cyclodextrin, dextrose, crospovidone, polydextrose, trehalose, maltose, maltitol, mannitol, maltodextrin, sorbitol, inulin, xylitol, erythritol, fumaric acid, glyceryl palmitostearate, lactose in particular agglomerated α-lactose-monohydrate [Ph.Eur./USP-NF/JP] (Tablettose®), hydrogenated vegetable oils, isomalt, kaolin, lactitol, triglycerides, particularly medium-chain triglycerides, polymethacrylate, and simethicone as well as derivatives or mixtures thereof, particularly preferred are lactose, in particular lactose monohydrate, microcrystalline or silicified or silicified microcrystalline cellulose, calcium hydrogenophosphate, starch glycolate, and crospovidone.

Examples of release modifying agents are gums such as guar gum, gum acacia, xanthan gums, alginates such as sodium alginate, glycerol monooleat, and castor oil. A wide variety of other possible agents are known by the skilled person.

Exemplary disintegrants which may be preferably used are alginic acid and salts thereof including calcium, sodium, magnesium, carboxymethylcellulose calcium, carboxymethylcellulose sodium, powdered cellulose, chitosan, colloidal silicon dioxide (e.g. highly dispersed types of colloidal silicon dioxide such as Aerosil®, Cab-O-Sil®), crospovidone, croscarmellose sodium, docusate sodium, guar gum, hydroxypropyl cellulose, particularly low-substituted hydroxypropyl cellulose, hydroxypropyl starch, magnesium aluminum silicate, methylcellulose, micocrystalline cellulose, polacrilin potassium, crosslinked povidone, sodium starch glycolate, starch, undried maize starch as well as derivatives or mixtures thereof, particularly pregelatinized starch, crosslinked povidone and undried maize starch.

An anti-tacking agent, anti-sticking agent, glidant or agent to improve flowability (flow control agents) can be used to improve powder flow properties prior to and during the manufacturing process and to reduce caking. A lubricant or agglomeration inhibitor can be used to enhance release of the dosage form from the apparatus on which it is formed, for example by preventing adherence to the surface of an upper punch ("picking") or lower punch ("sticking"). Among this group of excipients may be exemplarily mentioned boric acid, calcium silicate, cellulose, particularly powdered cellulose, anhydrous colloidal silica, DL-leucine, magnesium silicate, magnesium trisilicate, talc, silicon dioxide, starch, tribasic calcium phosphate, glyceryl behenate, magnesium oxide, mineral oil, poloxamer, polyvinyl alcohol, hydrogenated oils such as hydrogenated vegetable oils, hydrogenated castor oil, kaolin, (light) mineral oil, canola oil, triglycerides, such as medium-chain triglycerides, myristic acid, palmitic acid, polyethylene glycols (all types at different molecular weights of PEGs), benzoate such as sodium or potassium benzoate, sodium chloride, sodium lauryl sulfate, magnesium lauryl sulfate, sodium acetate, sodium benzoate, sodium fumarate, sodium oleate, sodium stearyl fumarate, talc, stearic acid, macrogol, like macrogol 400 or 6000, polyoxyl-40-stearate, waxes as well as derivatives or mixtures thereof.

Exemplarily mentioned acidifying agents or acidulants are, lactic acid, tartaric acid, fumaric acid, malic acid, and monobasic sodium phosphate as well as derivatives or mixtures thereof, preferably fumaric acid.

An example for a pharmaceutically acceptable crystallization retarder or modifier is raffinose, other excipients that can be used in this regard are for example other sugars and sugar alcohols, water soluble polymers or surfactants.

Preferable sweeteners are acesulfame potassium, alitame, aspartame, dextrose, erythritol, fructose, glycerin, inulin, isomalt, lactitol, liquid glucose, maltitol, maltose, mannitol, neospheridin dihydrochalcone, polydextrose, saccharin, saccharin sodium, sodium cyclamate, sorbitol, sucralose, sucrose, thaumatin, trehalose, and xylitol as well as derivatives or mixtures thereof.

Exemplary solubilizers are cyclodextrins, glycerin monostearate, lecithin, meglumine, poloxamers, polyethylene alkyl ethers, polyoxyethylene alkyl ethers, polyoxyethylene castor oil derivatives, polyoxyethylene sorbitan fatty acid esters, polyoxyethylene stearates, povidone, 2-pyrrolidone, sodium bicarbonate, sorbitan esters, stearic acid, and sulphobutylether as well as derivatives or mixtures thereof.

Exemplary colouring agents are preferably selected from beta-carotene, indigo carmine, iron oxides, preferably iron oxide yellow, sunset yellow, FCF, tartrazine, titanium dioxide as well as derivatives or mixtures thereof.

The taste masking agents are exemplarily selected from carbohydrates such as monosaccharides or disaccharides, ethyl lactate, ethyl maltol, ethyl vanillin, fumaric acid, leucine, malic acid, maltol, menthol, phosphoric acid, propylene glycol, sodium acetate, sodium lactate, thymol, meat flavour such as artificial beef flavour as well as derivatives or mixtures thereof, particularly preferred are dry meat flavour and vanillin.

Exemplary pH control or adjusting agents which are preferably used may be selected from glacial acetic acid, ammonia solution, diethanolamine, meglumine, sodium citrate dihydrate and also commonly known acidifying agents and buffering agents.

Exemplarily mentioned plasticizers are citrates such as acetyltributyl citrate, acetyltriethyl citrate, tributyl citrate, triethyl citrate, benzyl benzoate, castor oil, phthalates such as cellulose acetate phthalate, dibutyl phthalate, diethyl phthalate, dimethyl phthalate, hypromellose phthalate, polyvinyl acetate phthalate, dimeticon, fractionated coconut oil, chlorbutanol, dextrin, sebacate such as dibutyl sebacate, glycerine, glycerine derivatives such as glycerine monostearate, glycerine triacetate (triacetin), acetylated monoglyceride, mannitol, mineral oil, lanolin alcohols, palimitic0 acid, 2-pyrrolidone, sorbitol, stearic acid, triethanolamin, polyethyleneglycols (all types of PEGs of different molecular weights), propylene glycol as well as derivatives and mixtures thereof. Preferred plasticizers which may be used are acetylated monoglyceride, acetyltributyl citrate, acetyltriethyl citrate, dibutyl phthalate, dibutyl sebacate, diethyl phthalate, dimethyl phthalate, tributyl citrate, triethyl citrate, polyethylene glycols (all types of PEGs of different molecular weigths), and propylene glycol.

Surfactants are e.g. selected from anionic, cationic or nonionic species such as docusate sodium, emulsifying wax, self-emulsifying glyceryl monooleate, sodium lauryl sulfate, benzethoniumchloride, cetrimide, cetylpyridinium chloride, sodium lauryl sulfate, chlorhexidine, lauric acid, paraben series, sorbic acid, polyoxyethylene alkyl ethers, polyoxyethylene castor oil derivatives, polyoxyethylene sorbitan fatty acid esters, polyoxyethylene stearates, polysorbate, sorbitan esters and triethyl citrate, as well as derivatives and mixtures thereof.

Exemplary emulsifying agents are acacia, carbomers, carrageenan, propylene glycol alginate, hydroxypropyl cellulose or starch, hypromellose, palmitic acid, pectin, poloxamer, sorbitan esters, sunflower oil, tragacanth, and xanthan gum as well as derivatives and mixtures thereof.

The above listing is not intended to be of limitative character, the skilled person is familiar with further examples. As a matter of course also other pharmaceutical acceptable formulating agents in form of excipients, additives, carriers, technological adjuvants suitable in pharmaceutical formulations may be present. The term "excipients" or "additives" or "adjuvants" or the like as understood in the present invention shall mean any known suitable auxiliary compound which may be used in pharmaceuticals in order to provide one or more functionalities to the pharmaceutical tablet formulation according to the present invention. It belongs to the skill of the formulator that an excipient may have more than one function at the same time so that this excipient may form part of different categories. For example corn starch may impart several functions at the same time such as swelling polymer, filler, glidant, and the like. However, the skilled person knows the several functions and is able to select the excipient(s) according to the intended use thereof. The requirements are known by the skilled person.

The pharmaceutically acceptable excipients for the tablet formulation are in general present in order to promote manufacture, flow properties, compressibility, appearance and/or taste of the preparation. In the present invention the selection of the tablet excipients are primarily based on the main criteria to make the dissolution of pimobendan as rapid as possible and to further stabilize the instable ACE-inhibitor, preferably benazepril or a pharmaceutically aceptable salt as much as possible.

In a particularly preferred embodiment these excipients are incorporated in the tablet matrix (extra-granular phase) only, where pimobendan or a pharmaceutically acceptable salt thereof is present. A reason for this purpose is that instable ACE-inhibitors such as benazepril and its salts are more sensitive to moisture and excipients than pimobendan and its salts. Additional excipients may be present in the carrier core particles, but this is not always required. Furthermore, the first, second and any additional layer may contain one or more excipients, but this is not always necessary.

According to the present invention it has been surprisingly found that some excipients or a combination of several excipients has/have disadvantages or advantages in the pharmaceutical tablet formulation:

It has been found that meat flavour, for example dry meat flavour, citric acid and magnesium stearate have a negative impact on the stability of the instable ACE-inhibitor such as benazepril or the pharmaceutically aceptable salt thereof. That is, tablet mixtures using citric acid, dry meat flavour and/or magnesium stearate lead to instability and increased decomposition of benazepril or the pharmaceutically aceptable salt thereof. As a result, the selection of excipients is most preferably performed taking the following into account:

The excipients citric acid, magnesium stearate and meat flavour, for example dry meat flavour, should preferably not be present in the granules. Preferably the presence of citric acid and magnesium stearate in the pharmaceutical tablet formulation should be avoided completely.

It is highly desirable to have one or more pharmaceutically acceptable organic acids in the tablet matrix (extra-granular phase) together with pimobendan or a pharmaceutically acceptable salt thereof because the acid possesses a good solubilising characteristic and creates an acidic microclimate. Thus, the acid improves the dissolution of pimobendan and also enhances the release of the instable ACE-inhibitor such as benazepril from the polymer matrix present in the coating layer(s). In fact, it is common practice to circumvent the problem of pH dependent solubility by including ingestible organic acids in the formulation. By creating an acid microclimate and by utilising the tendency of pimobendan to form a supersaturated solution, the acid allows an adequate level of pimobendan solubility to be achieved. However, it has been found that citric acid clearly increases the destabilisation of instable ACE-inhibitors such as benazepril. Therefore, in case the tablet matrix comprises as acidifying agent one or more pharmaceutically acceptable organic acids, advantageously, citric acid should be excluded and preferably replaced by another pharmaceutically acceptable organic acid, such as tartaric acid, malic acid or fumaric acid, preferably fumaric acid. These acids, preferably fumaric acid are able to create an acidic microclimate and thus enhance the dissolution of pimobendan, but unlike citric acid, theses acids such as fumaric acid are less detrimental to the stability of any instable ACE-inhibitor such as benazepril or a pharmaceutically acceptable salt thereof.

Further, in case the tablet matrix comprises one or more lubricants, it is advantageous to eliminate magnesium stearate and preferably replace it by another lubricant, preferably stearic acid. It has been found that magnesium stearate should preferably be replaced by stearic acid because the stability of the ACE-inhibitor, preferably benazepril, in the presence of stearic acid is higher than in the presence of magnesium stearate.

Besides, although meat flavour has a destabilizing effect on ACE-inhibitors such as benazepril, it is undesirable to leave it out or replace it due to the use of the formulation in the veterinary medical sector. Therefore, it is most preferred to assure that the instable ACE-inhibitor, preferably benazepril, or a pharmaceutically acceptable salt thereof has no direct contact with the meat flavour. Therefore, the meat flavour is preferably not in the same layer as the active substance benazepril. From this point of view, providing a second layer between the first pharmaceutically active substance or its pharmaceutically acceptable salt and the tablet matrix containing the meat flavour has a further advantage.

According to a preferred embodiment of the present invention the first pharmaceutically active substance is a pharmaceutically acceptable salt of an instable ACE-inhibitor, preferably of benazepril, even more preferred benazepril hydrochloride, and the second pharmaceutically active substance is pimobendan.

The first and second pharmaceutically active substances are contained in an amount suitable for exhibiting the desired pharmacological activities of each medicament, respectively, which are known and vary in accordance with the medication. In order to determine the optimum dose of each of the two active substances, respectively, various basic conditions have to be taken into consideration such as for example the age and body weight of the animal patient, the nature and stage of the disease and the potency of each compound. This is deemed to be within the capabilities of the skilled man, and the existing literature on the components can be consulted in order to arrive at the optimum dose. The following doses may be preferably used: 1.25 mg, 2.5 mg, 5.0 mg, and 10.0 mg pimobendan or a pharmaceutically acceptable salt thereof; 2.5 mg, 5.0 mg, 10.0 mg, and 20.0 mg instable ACE inhibitor such as benazepril or a pharmaceutically acceptable salt thereof.

In the pharmaceutical tablet formulation according to the present invention the ratio of the first pharmaceutically active substance to coating and/or matrix forming polymer, preferably a polymer on methacrylic acid basis, in the first layer is from about 0.5 to 2:1 to 4, preferably about 0.75 to 1.75:1.25 to 3, more preferably 0.75 to 1.25:1.25 to 2.5, even more preferred about 1:2.

Furthermore, the ratio of the first pharmaceutically active substance to coating and/or matrix forming polymer, preferably a polymer on methacrylic acid basis, in the first and second layers together is from about 0.5 to 2:4 to 16, preferably about 0.75 to 1.75:5 to 12, more preferably about 0.75 to 1.5:6 to 10, even more preferred about 1:8.

It should be noted that the ranges of values given herein expressly include all the numerical values, both whole numbers and fractions, within the ranges as specified.

According to a preferred embodiment of the present invention the pharmaceutical tablet formulation is a chewable tablet. The tablet of the present invention can be of any suitable size and shape, for example round, oval, polygonal or pillow-shaped, and optionally bear non-functional surface markings. The tablet formulation can be divisable or not divisable, preferably the tablet is divisible into two or more pieces. As a charcateristic of the new formulation the functionality and release characteristics are not affected by the division.

The present invention is also directed to granules comprising carrier core particles coated with a layer containing an instable ACE-inhibitor or a pharmaceutically acceptable salt thereof, preferably benazepril or a pharmaceutically acceptable salt thereof, as a first pharmaceutically active substance and a coating and/or matrix forming polymer, preferably a polymer on a methacrylic acid basis (first layer). The granules according to the invention can be administered as granules or being further processed into capsules that can be administered to the animal. The granules may form part of the pharmaceutical tablet formulation or may be administered separately or in another suitable dosage form. Therefore, the granules may be administered directly or the granules may be filled in capsules or in sachets or may be processed into tablets.

Furthermore, the granules containing the first pharmaceutically active substance, i.e. an ACE inhibitor as already disclosed, may be part of a combination preparation. Such a combination preparation may comprise a first dosage form, that is the granules according to the present invention, and a second dosage form containing one or more pharmaceutically active substances which may be combined with the ACE inhibitor contained in the granules. The combined preparation may be intended for simultaneous, separate or seqeuntial use. The second dosage form may be any suitable dosage form known in the art such as granules, tablets, capsules or the like. The pharmaceutically active substances present in the second dosage form may be selected from a variety of possible substances, preferably the group of pharmaceutically active substances comprises PDE III inhibitors such as pimobendan, loop diuretics, potassium sparing diuretics, other diuretics than the previously mentioned, beta-blockers, calcium channel blockers, funny-channel blockers, renin antagonists, angiotensin antagonists, DPP4 inhibitors, antiarrhythmic agents, aldosterone antagonists, xanthine derivatives, arterial dilators, venodilators, positive inotropic agents, and anticoagulating agents. Other pharmaceutically active substances may be used, too.

The above explanations and disclosure, particularly with regard to the material of the carrier core particles and the polymer on methacrylic basis, apply here with regard to the granules, too.

The granules of the present invention comprise the coated carrier core particles as described above and an additional layer containing at least one coating and/or matrix forming polymer, preferably a polymer on methacrylic acid basis (second layer).

According to another embodiment of the invention the granules of the present invention may optionally comprise the coated carrier core particles additionally coated with a layer containing at least one coating and/or matrix forming polymer, preferably a polymer on methacrylic acid basis (second layer).

As already described, one or more optional intermediate layers may be present, but are not of essential character.

Typically, the granules exhibit a particle size distribution where ≥90% of the particles have a diameter of 125-750 µm and/or 50-80% of the particles have a diameter of 250-500 µm.

In the carrier core particles, the first and second layer of the granules may additionally comprise one or more excipients as already discussed. The carrier core particles, the first and optional additional layers of the granules may additionally comprise one or more excipients as already discussed.

Therefore, the pharmaceutical tablet formulation comprises the granules (carrier core particles and at least one layer) and the extra-granular phase (tablet matrix), the first pharmaceutically active substance being present in the granules whereas the second pharmaceutically active substance is present in the extra-granular phase.

The granules which have been developed serve a double purpose in that they mask the bitter taste of an instable ACE-inhibitor but also have a protective purpose for the instable ACE-inhibitor or its salts, i.e. the granules provide an instable ACE-inhibitor in stablised form. Therefore, in a preferred embodiment the granules serve to better mask the bitter taste of benazepril and also have a protective purpose for benazepril or its salts that is the granules provide benazepril hydrochloride in a more stable form than benazepril hydrochloride alone.

Subject of the present invention is also a process for preparing the pharmaceutical tablet formulation according to the present invention comprising
  fluid bed coating using a coating solution, preferably an alcohol containing solution, comprising an instable ACE-inhibitor or a pharmaceutically acceptable salt thereof, preferably benazepril or a pharmaceutically acceptable salt thereof, and at least one coating and/or matrix polymer, preferably a polymer on methacrylic acid basis, using carrier core particles to obtain a coated granulate;
  a second fluid bed coating using a further coating solution, preferably an alcohol containing solution, comprising at least one coating and/or matrix polymer, preferably a polymer on methacrylic acid basis, to obtain a double coated granulate;
  mixing pimobendan or a pharmaceutically acceptable salt thereof with the excipient/s of a tablet matrix to obtain a premix;
  optionally sieving the obtained coated granulate through a screen;

mixing the coated granulate and the premix to obtain a blend;

mixing the blend with one or more lubricants and/or glidants to obtain a final blend, and compressing said final blend to a tablet.

It is a matter of course that also other formulation procedures to arrive at the pharmaceutical tablet formulation may be used. The process according to the present invention represents only one alternative possible, the skilled person is aware of other formulation procedures.

Subject of the present invention is also a process for preparing the granules according to the present invention comprising fluid bed coating using a coating solution, preferably an alcohol containing solution, comprising an instable ACE-inhibitor or a pharmaceutically acceptable salt thereof, preferably benazepril or a pharmaceutically acceptable salt thereof, and at least one coating and/or matrix polymer, preferably a polymer on methacrylic acid basis, using carrier core particles to obtain a coated granulate;

a second fluid bed coating using a further coating solution, preferably an alcohol containing solution, comprising at least one coating and/or matrix polymer, preferably a polymer on methacrylic acid basis, to obtain a double coated granulate;

optionally sieving the obtained coated or double coated granulate through a screen.

It is a matter of course that also other formulation procedures to arrive at the granules may be used. The process according to the present invention represents only one alternative possible, the skilled person is aware of other formulation procedures.

In the following the inventive process shall be discussed in detail.

At first, a fluid bed coating is performed using a coating solution (first layer). The coating solution is preferably an alcohol containing solution comprising an instable ACE-inhibitor, preferably benazepril or a pharmaceutically acceptable salt thereof and at least one coating and/or matrix polymer, preferably a polymer on methacrylic acid basis. The coating solution used in the first coating step is produced immediately prior to use, the instable ACE-inhibitor, preferably benazepril or a pharmaceutically acceptable salt thereof, is dissolved and subsequently the coating and/or matrix polymer is added and dissolved during optionally mixing or vice versa. Alternatively two solutions are produced separately, one solution comprising the instable ACE inhibitor, preferably benazepril or a pharmaceutically acceptable salt thereof, and the other solution comprising at least one coating and/or matrix polymer, preferably a polymer on methacrylic acid basis, and both solutions are combined prior to performing the first coating step.

The used solvent is any suitable solvents or mixtures thereof, perferably physiologically acceptable solvent or solvent mixture, e.g. a low-boiling alcohol, ester, ketones or a respective mixture with water. A number of solvents are suitable. Readily volatile solvents are preferred. Exemplarily mentioned solvents are methanol, ethanol, 1-propanol, isopropanol, butanol, iso-butanol, 2-butanol, tert-butanol, ethyl acetate, ethyl formate, acetone and the like as well as mixtures thereof with or without water.

Subsequently, a second fluid bed coating step is conducted (second layer). The second fluid bed coating step is an optional process step which is performed in case a second layer shall be present on the first layer. In the second coating step a further coating solution is used, preferably an alcohol containing solution comprising at least one coating and/or matrix polymer, preferably a polymer on methacrylic acid basis. The polymer on methacrylic acid basis is a polymer which belongs to the polymethacrylates such as methaycrylic acid-ethyl acrylate copolymer (1:1) as already described. Polymethacrylate polymer(s), which is(are) soluble under acidic conditions, but insoluble under neutral or basic conditions is(are) preferred. The mentioned polymer is used alone or in combination of two or more polymers. Commercially available products are the polymers from the Eudragit® series from the company Rohm, Darmstadt, Germany. Particularly preferred are polymers on methacrylic acid basis, which belong to the polymethacrylates such as methaycrylic acid-ethyl acrylate copolymer (1:1), e.g. polymers belonging to the commercially available products Eudragit® E or Eudragit® EPO.

The coating and/or matrix polymer(s) used in the first layer may be the same or different from the coating and/or matrix polymer(s) used in the second layer. According to a preferred embodiment the polymethacrylate polymer(s) used in the first layer may be the same or different from the polymethacrylate polymer(s) used in the second layer. According to a further preferred embodiment the polymer on methacrylic acid basis in the two layers is the same, while other polymers can be present in either or both layer(s). In a more preferred embodiment only one polymer on methacrylic acid basis is used and the polymer in the first and second layer is the same.

In the first coating step the first layer as already described is applied on the carrier core particles to obtain a coated granulate. In the second coating step the second layer as already described is applied on the coated carrier core particles to obtain a double coated granulate. In the second layer the coating and/or matrix polymer, preferably polymer(s) on methacrylic basis, is present but not the instable ACE-inhibitor or a pharmaceutically acceptable salt thereof. This second layer is present in order to increase the effectivity of the protecting and masking performance because the bitter tasting first pharmaceutically active substance is then no longer present on the outer or second layer.

The expression "taste masking" according to the present invention is understood to mean the protection of the active substance against the immediate action of saliva and its constituents upon oral administration as well as against the sense of smell and taste of the animal. A masked active substance shall have a neutral taste and/or smell and/or a taste acceptable to companion animals. This is confirmed by a free-choice acceptance test.

During the formation of the coating(s) on the carrier core particles, granules are formed, the coating and/or matrix polymer(s), preferably the polymer(s) on methacrylic acid basis act(s) as a type of binder.

Any type of fluidised bed process is suitable according to the process of the present invention. The coating step(s) may be performed in a fluid bed granulator or other suitable apparatus. A top-spray fluid bed process is preferred. The conditions and parameters of the fluid bed coating step(s) such as the spray rate, atomization pressure, spray nozzle diameter, inlet air temperature, product temperature and the like belong to the skill of the expert who is readily able to determine and adjust these conditions and parameters based on some experimentation.

It is a matter of course that the granules may further contain one or more excipients as already described. However, due to the sensitive character of the instable ACE-inhibitor, preferably benazepril and its pharmaceutically acceptable salt, these excipients should be carefully selected, if any.

The further steps are omitted if the granules shall be produced. If the pharmaceutical tablet formulation shall be produced the further steps are carried out.

In the next step pimobendan or a pharmaceutically acceptable salt thereof is mixed with the excipient/s of a tablet matrix to obtain a premix. The one or more useful excipients are already discussed above. The mixing may be performed in any suitable apparatus. Additionally micronizing of the second active substance pimobendan has a positive impact on its dissolution kinetic.

Then the coated or double coated granulate and the premix are mixed to obtain a blend. The coated or double coated granulate are sieved through a screen prior to the addition to the premix or the coated or double coated granulate are mixed with the premix without any further sieving. The mesh size is preferably selected in the range of from about 0.5 to 2 mm.

Subsequently, the blend is mixed with one or more lubricants and/or glidants to obtain the final blend. According to a preferred embodiment the ratio of granules (carrier core particles+first layer containing first pharmaceutically acceptable substance+optional second layer) to extra-granular material (tablet matrix+second pharmaceutically substance) is about 10:90 to about 90:10, preferably about 20:80 to about 80:20 (w/w), preferably 50:50 (w/w), in the pharmaceutical tablet formulation.

Then, the final blend is compressed to a tablet using a commonly applied tablet compressing device.

It is preferred that the coated carrier core particles meet certain characteristics in order not to affect the release performance when later processed to tablets.

For example, it is preferred that the granulate grains or granules should predominantly undergo plastic deformation upon compression. Furthermore, it is preferred that the polymer coating is sufficiently flexible so that a deformation will not cause any major rupture or brittle fracture. Finally, it is also preferred that the carrier core particles of the granulate grains or granules only show minimal/negligible swelling.

The carrier core particles are selected from the materials as already described, whereby lactose, particularly agglomerated α-lactose-monohydrate [Ph.Eur./USP-NF/JP] with a particle size distribution as follows: ≤20%<63 μm, 40-75%<180 μm, ≤85%<400 μm, and ≤97%<630 μm is preferred. Lactose such as spray dried or agglomerated lactose, with the characteristics described above is particularly suitable for use in the core because of its particle size, non-hygroscopicity, and the fact that it undergoes plastic deformation upon compression so that the core will not break into pieces in the tablet press. Therefore, lactose is a carrier material to be preferably used in the carrier core particles due to the following properties:

Lactose, particularly lactose monohydrate or spray dried or agglomerated lactose, is well suited to be used as carrier material because during the later tablet forming step lactose having an amorphous proportion shows a partly ductile performance. Thus, only little brittle fracture in the inner part of the carrier core particles coated with polymethacrylate polymer(s) is occurring. This is a particular advantage because snatchings could damage the polymer film and, therefore, the dissolving properties of the tablet are altered undesirably. A significantly changed substance release could result in a modified bioavailability whereby the formulations are no longer bioequivalent or a premature substance release in the mouth could occur and the masking of the bitter taste would be unsuccessful.

Furthermore, lactose, particularly lactose monohydrat, is particularly suitable as a non-swelling tablet excipient, because in case the granules containing polymer-ACE inhibitor-lactose come into contact with water, the polymer will interact with water and swell also in neutral pH-value so that water can penetrate by diffusion into the core of the granules. If the core of the granules would also tend to swell, the increasing swelling pressure inside the granules would result in a premature decomposition and a damage of the coating film. Thus, the active substance would be released prior to the intended time. Since lactose does not tend to swell, this unwanted effect is eliminated. Therefore, it is particularly preferred to use lactose alone as carrier core particle material. Besides lactose also other carrier materials are suitable. Preferably the carrier core particle material consists of lactose, such as lactose monohydrat, more preferably agglomerated lactose, or another alternative carrier material.

Further alternative carrier materials to be used are carbohydrates, sugar alcohols, such as mannitol, sorbitol, maltitol, glucose, non-pareil-seeds, calcium phosphate, cellulose, particularly preferable microcrystalline cellulose (MCC), and starch.

Cellulose and starch are also ductile deformable, but these materials tend to swell resulting in the described undesirable effect that the taste masking coating would be less effective.

Another carrier material which can be used is MCC pellets, which exhibit low swelling, and uniform size and surface structure.

The present invention is also directed to the use of the pharmaceutical tablet formulation according to the present invention or to the use of the granules according to the present invention for preparing a pharmaceutical veterinary medical composition which is suitable for preparing a pharmaceutical veterinary medical composition for preventing and/or treating heart diseases, disorders, or complications associated therewith, preferably selected from heart failure, congestive heart failure, increased size of the heart, and hypertension, particularly the prevention and/or the treatment of congestive heart failure originating from dilated cardiomyopathy or valvular insufficiency (mitral and/or tricuspid regurgitation), in mammals, preferably in pet animals, more preferably in dogs, cats, and rodents, most preferably in dogs.

The mammals according to the invention is preferably a mammal selected from the group consisting of dogs, cats and rodents such as rabbits, most preferably dogs.

The tablets which are provided may be packed in bottles or blisters well known in the art. Among such blisters are such being made of polyvinylchloride and/or polyvinylidene chloride or aluminum. Aluminum blisters are preferred due to the better barrier protection to moisture. Bottles are made of poylpropylene or polyethylene for example. Other conventional packaging materials are possible, too.

The package is designed particularly user-friendly in order to ease the administration of different dosages and to simplify the observation of and adherence to the therapy. Therefore, the blister, for example, contains one dosage in one row having a specific colour intended for use in the morning and another dosage in another row having another specific colour intended for use in the evening. For safety reasons there are additional different symbols on the rows meaning that the tablets for administration in the morning have a bright colour code (such as yellow, orange, light red, etc) and a sun symbol, whilst the rows containing a tablet for evening administration have a dark colour (brown, dark blue, black etc.) and a half-moon symbol printed on it.

The pharmaceutical tablet formulation of the invention is packaged in a container, accompanied by a packag insert providing pertinent information such as, for example, dosage and administration information, contraindications, precautions, drug interactions, and adverse reactions.

Since the instable ACE-inhibitor, preferably benazepril and its salts are known to be highly moisture sensitive, the product stability is enhanced, for example, by reducing the initial moisture of the product before packaging and in the packed product. Therefore, the initial moisture of the product is reduced by optimizing the holding times and the storage conditions of the intermediate products, i.e. raw materials, granulate, extra-granular phase, final blend, unpacked tablets etc. The manufacturing can also be associated to a monitoring of the water content. As a precautionary measure, hygroscopic raw materials could be packed in protective packaging, and the intermediate products could be stored in protective containers with desiccant bags. Furthermore, the concentration of hygroscopic components of the formulation should be observed and reduced.

The invention described will now be illustrated by drawings. However, it is expressly pointed out that the drawings are intended solely as an illustration and should not be regarded as restricting the invention.

BRIEF DESCRIPTION OF THE DRAWINGS

In the drawings

FIG. 1 shows an exemplarily schematic illustration of the granules according to a preferred embodiment of the present invention. The granules 100, 110 are schematically shown. The carrier core particles 10 are enclosed by the first layer 20 which contains the instable ACE inhibitor, in the present example benazepril, or one of its salts and one or more coating and/or matrix forming polymers, e.g. one or more polymers on methacrylic acid basis. A predominantly ductile deformable carrier material is most convenient so that a brittle break of the particles does not occur and a damage of the first layer is prevented. Furthermore, a non-swelling carrier material is particularly appropriate, so that water cannot penetrate by diffusion into the core of the granules and cause swelling of the core. Thus, a premature release of the active substance is avoided. For example, lactose, particularly lactose monohydrat or spray dried lactose, more preferably agglomerated or spray dried lactose, is one of the well suited carrier materials. Other materials may be used just as well.

Furthermore, the one or more coating and/or matrix forming polymers, e.g. one or more polymers on methacrylic acid basis, in the first layer 10 are selected due to their characteristics, for example, so that the polymer coating is sufficiently flexible and a deformation can not cause any damage.

The second layer 30 comprises or consists of the one or more coating and/or matrix forming polymers, e.g. one or more polymers on methacrylic acid basis. More preferably the polymer is a cationic copolymer based on dimethylaminoethyl methacrylate copolymer (IUPAC name: poly(butyl methacrylate-co-(2-dimethyl-aminoethyl) methacrylate-co-methyl methacrylate) 1:2:1) such as Basic Butylated Methacrylate Copolymer Ph. Eur.

Figure 1:
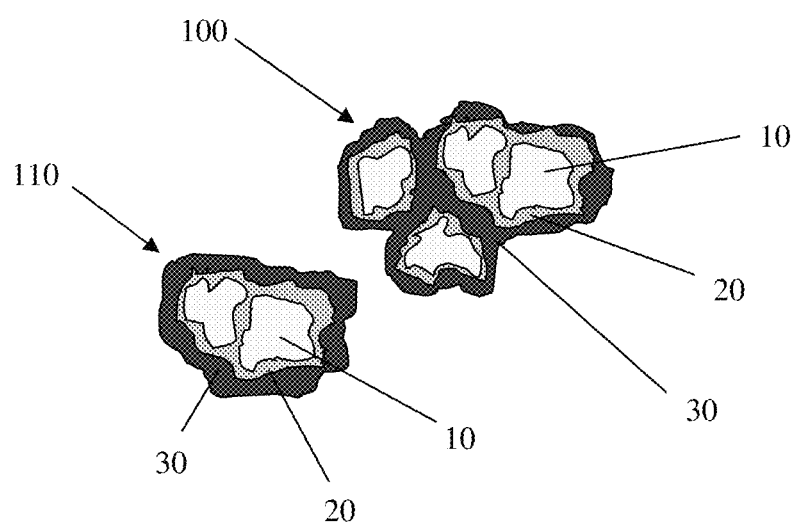
FIG. 1 shows an exemplarily schematic illustration of the granules according to a preferred embodiment of the present invention.

As FIG. 1 shows, the formation of the first and second layers 10 and 20 on the carrier core particles result in stabilized granules 100, 110, the polymer(s) serves as an adhesive and stabilizer between the particles meaning as a binder.

The granules 100, 110 of the present invention due to their composition and build-up, are able to mask the bitter taste of the ACE inhibitor and its salts and also have a protective purpose for the ACE inhibitor, that is the granules 100, 110 provide the ACE inhibitor in a more stable form than the ACE inhibitor per se.

As shown in FIG. 1, the granules 100, 110 can have different sizes, but typically, the granules exhibit a particle size distribution where ≤90% of the particles have a diameter of 125-750 µm.

Figure 2:
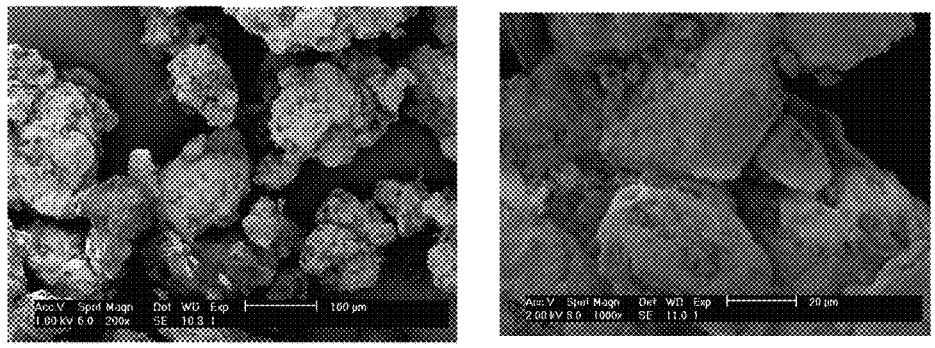
FIG. 2 shows scanning electron microscope (SEM) pictures of coated granules according to the present invention.
Figure 2:
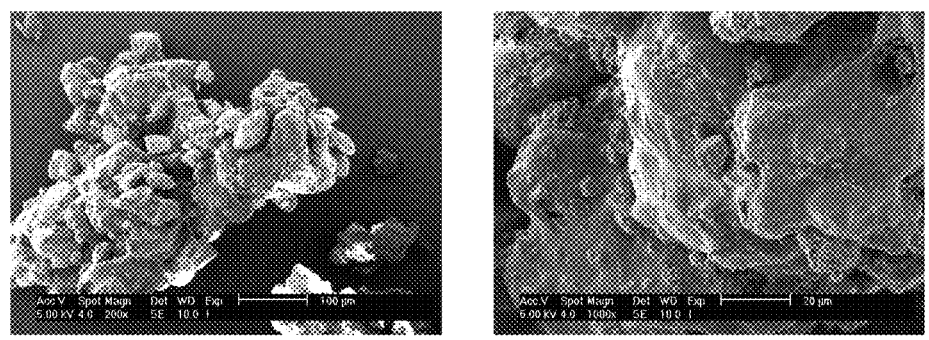
Figure 2:
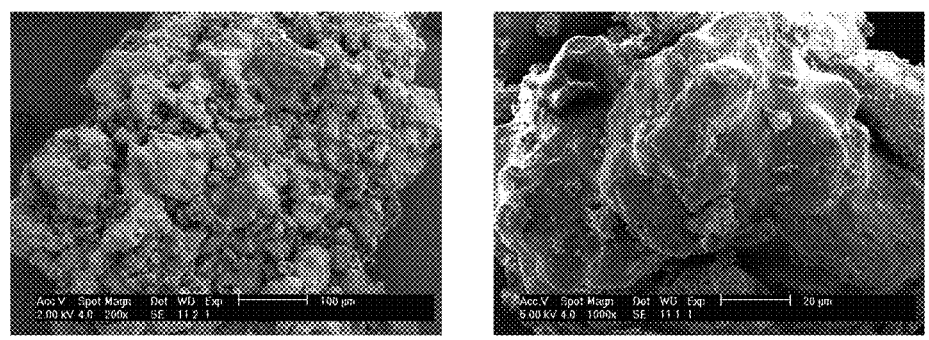

FIG. 2 shows SEM pictures of coated granules according to the present invention. There are provided 6 pictures: No. 1, No. 2 and No 3, with 2 pictures respectively. There are shown 3 different granules, the composition in detail is as follows:

Granules No. 1: Benazepril HCl 5 g; butylated methacrylate copolymer 80 g, agglomerated lactose 915 g
Granules No. 2: Benazepril HCl, 5 g; butylated methacrylate copolymer 80 g, agglomerated lactose 915 g
Granules No. 3: Benazepril HCl, 10 g; butylated methacrylate copolymer 80 g, agglomerated lactose 915 g The magnification of the pictures is as follows: left: 200×, right: 1000×

Figure 3:
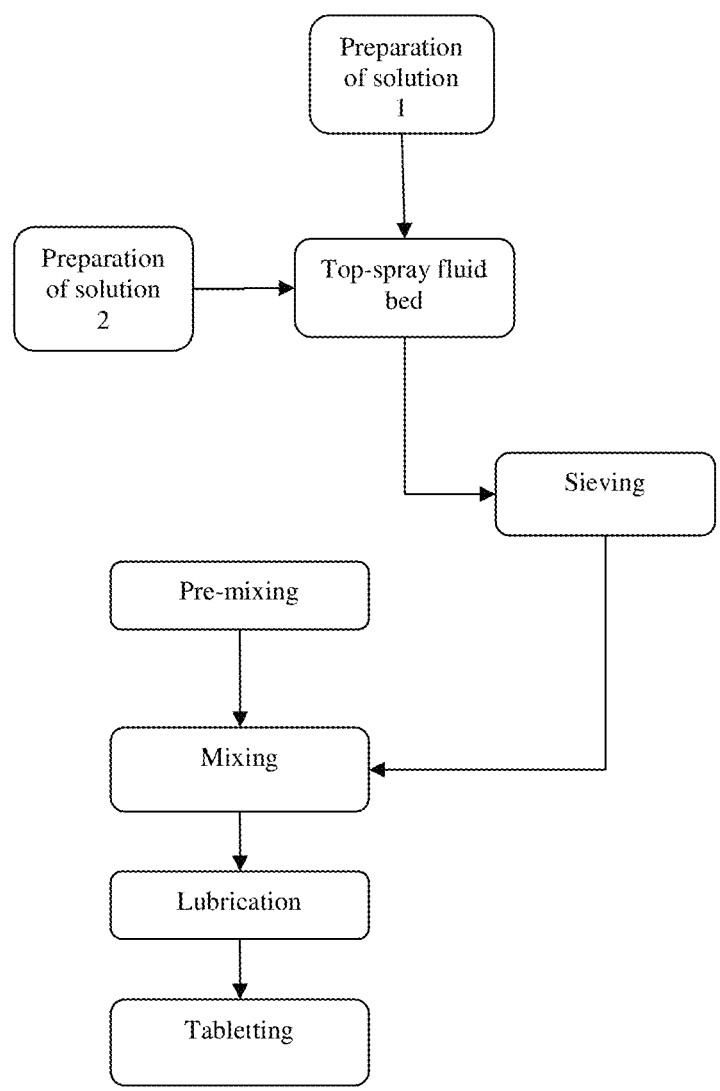
FIG. 3 represents a flow diagram illustrating a preferred method for the manufacturing of the pharmaceutical tablet formulation according to a preferred embodiment of the present invention.

FIG. 3 represents a flow diagram illustrating a preferred method for the manufacturing of the pharmaceutical tablet formulation according to a preferred embodiment of the present invention. The described method of manufacturing is not intended to limit the present invention, other processes are possible.

As derived from the flow diagram of FIG. 3, in the first step a fluid bed coating is performed using coating solution 1. The coating solution 1 is a solvent containing solution, whereby any suitable, pharmaceutically acceptable solvent containing solvent or solvent mixture, such as an alcohol-water mixture may be used. For example, the solvent may contain ethanol and water. Also the ACE inhibitor such as benazepril or a pharmaceutically acceptable salt is contained in coating solution 1. For example benazepril hydrochloride may be employed as first active substance. It is also possible to use another ACE inhibitor or another pharmaceutically acceptable salt thereof.

Furthermore, the polymer(s) is (are) any polymer or mixture of polymers as already described. In the present exemplarily described embodiment the polymer is on methacrylic acid basis, e.g. Basic Butylated Methacrylate Copolymer Ph. Eur. Also another polymer or a mixture of more polymers can be used.

Then, the coating solution 1, containing in the present case benazepril hydrochloride dissolved together with the at least one polymer on methacrylic acid basis such as Basic Butylated Methacrylate Copolymer Ph. Eur. in one or more solvents, for example ethanol/purified water, is sprayed onto the carrier core particles in a fluid bed apparatus. In the present example the carrier core particles are any of the carrier materials as described above. For example agglomerated lactose with a particle size $d_{50}$ of ca. 180 μm is used. However, other materials are also possible. The fluid bed apparatus may be any available device known by the skilled person. Preferably a top-spray fluid bed process is used. In an exemplary embodiment a top-spray fluid bed granulator of the company Glatt may be used. In the exemplary embodiment a layer containing benazepril hydrochloride and Basic Butylated Methacrylate Copolymer Ph. Eur. on the lactose particles is produced (first or inner layer).

According to the flow chart shown in FIG. 3 the second coating step is performed using coating solution 2. Coating solution 2 is again a solvent containing solution, whereby any suitable pharmaceutically acceptable solvent containing solvent or solvent mixture, such as an alcohol containing solution may be used, which for example, contains ethanol, purified water, and Basic Butylated Methacrylate Copolymer Ph. Eur. Also another solvent or mixture of solvents and another polymer, e.g. a polymer on methacrylic acid basis or mixture of polymers may be used. The coating and/or matrix forming polymer(s) such as a polymethacrylate polymer(s) used in the first layer is the same or different from the coating and/or matrix forming polymer(s) such as a polymethacrylate polymer(s) used in the second layer. According to the exemplarily described embodiment the polymer on methacrylic acid basis in the two layers is the same.

The coating solution 2 results in the formation of the second layer. The second layer is especially deposited in order to increase the effectivity of the masking performance because the bitter tasting active substance—in the present example benazepril hydrochloride—is then no longer present on the top surface of the particles.

After the spraying procedure, the solvent or solvent mixture may be removed carefully, e. g. by continuing to dry the granulate in the fluid bed apparatus.

The conditions and parameters of the fluid bed coating step(s) such as the spray rate, atomization pressure, spray nozzle diameter, inlet air temperature and product temperature belong to the basic knowledge of the skilled person. According to the exemplary embodiment described the coating solutions may be sprayed on the carrier core particles maintained at a product temperature range from 18° C. to 25° C. Then the obtained granules may be dried and sieved through a screen.

The further steps are omitted if the product to be produced is the granulate. The granules containing ACE inhibitor are well suited to be administered as granules or processed further into capsules or tablets. The granules may also form part of a combined preparation such as a kit of parts, wherein the ACE inhibitor present in the granules may be combined with one or more other pharmaceutically active substances provided in a separate administration form, e.g. also in form of granules or as tablets or capsules or the like.

If the pharmaceutical tablet formulation is to be produced the further steps are carried out.

In the next step according to the flow diagram of FIG. 3 pimobendan or a pharmaceutically acceptable salt thereof is mixed with the excipient/s of a tablet matrix to obtain a premix. The tablet matrix together with pimobendan or a pharmaceutically acceptable salt thereof forms the extra-granular fraction or phase of the pharmaceutical tablet formulation according to the present invention. The excipients may be selected from one or more of the above listed excipients preferably taking the specific particularities with regard to excipients citric acid, magnesium stearate and/or meat flavour as mentioned above into account.

The premixing may be performed in any suitable apparatus. For example a Rhönrad can be employed. Also any other mixing apparatus may be used.

Then, the coated granules and the premix are mixed to obtain a blend. The coated granules may be optionally sieved through a screen prior to the addition to the premix as already mentioned; the mesh size being preferably in the range of from about 0.5 to 2 mm.

Subsequently, the blend is mixed with one or more lubricants and/or glidants to obtain a final blend. Any lubricant and/or glidant known by the skilled person may be added but magnesium stearate should be preferably excluded. According to a preferred embodiment the ratio of granules (carrier core particles+first layer containing first pharmaceutically acceptable substance+optional second layer) to extra-granular material (tablet matrix+second pharmaceutically substance) is about 10:90 to about 90:10, preferably 20:80 to about 80:20 (w/w) in the pharmaceutical tablet formulation.

Then the final blend is compressed to a tablet in a common tablet compression apparatus.

The advantages of the present invention are manifold:

According to the present invention it is possible to combine two pharmaceutical active substances in one single dosage form, i.e. as combination drugs. The advantage of such a formulation is that the doses are fixed in this pharmaceutical formulation, available in certain fixed doses. In such a case the pharmaceutical formulation is called a "fixed-dose-combination". Such a type of formulation allows to ease the treatment and administration of the medication, the treatment of the sick animal is easier to be done. The pharmaceutical tablet formulation according to the present invention improves the medication compliance by reducing the pill burden to the animal holder. A further improvement relies on the better observation of and adherence to the therapy by decreasing the number of tablets to be administered. The lower number of tablets leads to a lower treatment failure rate, minimizes dosage mistakes and avoids confusions by false dose intake and slower development of resistance.

A synergistic combination of two active substances is provided wherein the combined activity exceeds the activity of the single active substances.

Furthermore, a single coating (first layer) is sufficient according to the present invention but a double coating assures excellent palatability by the animal.

According to the present invention it has been surprisingly found that meat flavour, citric acid and magnesium stearate have an unfavourable impact on the stability of the instable ACE inhibitor or the pharmaceutically aceptable salt thereof. It has been found that citric acid should preferably be replaced by tartaric acid, malic acid or fumaric acid because the stability of instable ACE inhibitor in the presence of acids such as tartaric acid, malic acid or fumaric acid is improved compared to citric acid. Furthermore, magnesium stearate should preferably be replaced by stearic acid because the stability of instable ACE inhibitor is likewise improved. In addition it is preferred to assure that the instable ACE inhibitor or a pharmaceutical acceptable salt thereof has no direct contact with the meat flavour. As a result, the careful selection of excipients supports the increased stability of the instable ACE inhibitor or a pharmaceutically salt thereof in the dosage form. Another result or technical advantage is that this keeps the incompatible ingredients physically separate without having to resort to complex production processes such as multi-layer tablets.

The specific composition and structure of the pharmaceutical tablet formulation of the present invention provides a number of additional benefits:

The granules provided are generally more uniform than powder and allow a more homogeneous tablet mass and higher dosage accuracy to be achieved. Furthermore, the granules which have been developed in order to better mask the bitter taste of the instable ACE inhibitor or its salts also have a protective purpose for the instable ACE inhibitor or its salts, the granules provide the ACE inhibitor in a more stable form than ACE inhibitor alone.

Furthermore, the polymers present in the granules at the same time mask its bitter taste. Furthermore, the polymer(s) present in the pharmaceutical tablet formulation of the present invention is (are) employed to optimize the release performance so that the instable ACE inhibitor and the active substance pimobendan are immediately dissolved in the stomach and not in the mouth of the animal. Moreover, the polymer provides protection of the active substances from moisture. Finally the polymer(s) function as a binder to bind the active substance to the carrier material.

Also granules are provided which may be administered as stand-alone granules for the ACE inhibitor or any salt thereof or be compressed with suitable excipients to a mono tablet showing the flexibility and versatility of the particles. The granules containing ACE inhibitor are well suited to be administered as granules or processed further into capsules or tablets. Furthermore, it has been observed that the shape and size of the granules according to the present invention provide an excellent mouth feeling so that animals willingly accept the intake of such granules as medicament. According to a further preferred embodiment of the present invention the granules may be administered directly or the granules may be filled in capsules or in sachets.

Furthermore, the granules containing the first pharmaceutically active substance, i.e. an ACE inhibitor as already disclosed, may be part of a combination preparation for simultaneous, separate or sequential use. The first dosage form may be the granules and the second dosage form may contain one or more other pharmaceutically active substances which may be combined with an ACE inhibitor. The second dosage form may be any usual dosage form known in prior art. The pharmaceutically active substance(s) present in the second dosage form may also be arbitrarily selected from a variety of possible substances, preferably the group comprises PDE III inhibitors such as pimobendan, loop diuretics, potassium sparing diuretics, other diuretics than the previously mentioned, beta-blockers, calcium channel blockers, funny-channel blockers, renin antagonists, angiotensin antagonists, DPP4 inhibitors, antiarrhythmic agents, aldosterone antagonists, xanthine derivatives, arterial dilators, venodilators, positive inotropic agents, and anticoagulating agents. Also other pharmaceutically active substances may be used.

The invention described will now be illustrated by Examples. However, it is expressly pointed out that the Examples and description are intended solely as an illustration and should not be regarded as restricting the invention.

Unless otherwise stated, percentages specified are always percent by weight.

EXAMPLES

I. Process of Production

Example 1—Pharmaceutical Tablet Formulation Containing a First And a Second Layer In the following a preferable general procedure to manufacture chewable tablets according to the present invention is exemplarily described. However, the process steps and components are not intended to be of limitative character:

The coating solutions were prepared by dissolving the cationic copolymer Basic Butylated Methacrylate Copolymer Ph. Eur. in an organic solvent, e.g. an ethanol 99%/water mixture. Then, in order to produce coating solution 1 benazepril hydrochloride was dissolved in an aliquot of said coating solution. Coating solution 1 contains Basic Butylated Methacrylate Copolymer Ph. Eur., ethanol 99%, purified water, and benazepril hydrochloride. Coating solution 2 is the remaining portion which only contains Basic Butylated Methacrylate Copolymer Ph. Eur., ethanol 99%, and purified water. The coating solutions were subsequently sprayed on the carrier core particles consisting of α-lactose monohydrate, in the present case agglomerated α-lactose monohydrate, maintained at a defined product temperature range from 18° C. to 25° C. in a top-spray fluid bed granulator of the company Glatt GPCG30.

The spray coating parameters were as follows:

Spray rate: 140 to 250 g/min

Spray time: about 60 min

Atomization pressure: 1.5-2.0 bar

Product temperature: 18-25° C.

Inlet air temperature: 35-45° C.

Inlet air flow rate: 400-600 m$^3$/h

Drying time: until a product temperature of 42° C. is reached

The first spraying step corresponded to the spraying of a combined Basic Butylated Methacrylate Copolymer Ph. Eur./benazepril hydrochloride solution, whereas the second one corresponded to the deposition of pure Basic Butylated Methacrylate Copolymer Ph. Eur. solution.

The obtained granules were dried and sieved through a screen.

The desired excipients in the defined amounts and pimobendan which will form together the extra-granular fraction (tablet matrix) were premixed in a free-fall tumbler (10 min; 10 rpm) and the granules were added. The granules and the extra-granular fraction were mixed in a ratio of granules to extra-granular material of about 50:50 (w/w) in a free-fall tumbler (20 min, 10 rpm). Then, the lubricant micronized stearic acid was mixed into the mixture (5 min, 10 rpm). The mixture was tabletted into tablets of 500 mg, 1000 mg, 2000 mg, or 4000 mg weight on a rotary tablet press.

The tablet formulations of four dosage strengths prepared were as follows:

1.25 mg/2.5 mg pimobendan/benazepril HCl for a chewable tablet of 500 mg;

2.5 mg/5.0 mg pimobendan/benazepril HCl for a chewable tablet of 1,000 mg;

5.0 mg/10.0 mg pimobendan/benazepril HCl for a chewable tablet of 2,000 mg;

10.0 mg/20.0 mg pimobendan/benazepril HCl for a chewable tablet of 4,000 mg.

The detailed tablet formulation compositions are given in the following table 1. All tablet sizes are based on the same tablet mixture, the different potencies are obtained by modifying the weight of the tablet. The ACE inhibitor used is benazepril hydrochloride and the PDE III inhibitor is pimobendan, however, any other instable ACE inhibitor and any other PDE III inhibitor may be used.

TABLE 1 tablet compositions

| | Dosage strength | | | | |
|---|---|---|---|---|---|
| | 1.25/2.50 | 2.5/5.0 | 5.0/10.0 | 10.0/20.0 | |
| | Tablet weight | | | | |
| | 0.5 g | 1.0 g | 2.0 g | 4.0 g | |
| Ingredients | mg/tablet | mg/tablet | mg/tablet | mg/tablet | % |
| Benazepril hydrochloride | 2.50 | 5.00 | 10.00 | 20.00 | 0.5 |
| Eudragit ® EPO | 20.00 | 40.00 | 80.00 | 160.00 | 4.0 |
| Monohydrate lactose Tablettose ® 80 agglomerated α-lactose-monohydrate [Ph. Eur./USP- NF/JP] | 370.25 | 740.50 | 1481.00 | 2962.00 | 74.05 |
| Pimobendan | 1.25 | 2.50 | 5.00 | 10.00 | 0.25 |
| Dry Meat Flavour | 50.00 | 100.00 | 200.00 | 400.00 | 10.0 |
| Colloidal silica, anhydrous | 2.50 | 5.00 | 10.00 | 20.00 | 0.5 |
| Maize starch, undried | 25.00 | 50.00 | 100.00 | 200.00 | 5.0 |
| Fumaric acid | 10.00 | 20.00 | 40.00 | 80.00 | 2.0 |
| Crospovidone | 10.00 | 20.00 | 40.00 | 80.00 | 2.0 |
| Iron oxide yellow | 6.00 | 12.00 | 24.00 | 48.00 | 1.2 |
| Stearic acid, micronized | 2.50 | 5.00 | 10.00 | 20.00 | 0.5 |
| Total amount per tablet | 500.00 | 1000.00 | 2000.00 | 4000.00 | 100% |

[1]Organic solvent and purified water are removed from the granulate during the respective drying step

Example 2—Granules

Following the procedure according to example 1 granules according to the present invention have been produced, the steps wherein the tablet formation took place have been omitted. The detailed granulate compositions having only one layer (the first layer) coated on the carrier core particles are summarized in the following table 2 wherein different Eudragit® E: benazepril (E/B) ratios are used. The ACE inhibitor used is benazepril, however, any other instable ACE inhibitor may be used.

TABLE 2

Granulate compositions

| Dosage | D1 (E/B 5:1) | | D2 (E/B 2.5:1) | | D3 (E/B 1.25:1) | |
|---|---|---|---|---|---|---|
| Formula | ratio % | g/batch | ratio % | g/batch | ratio % | g/batch |
| Benazepril | 3% | 1 | 3% | 1 | 3% | 1 |
| Eudragit ® E | 12% | 5 | 6% | 2.5 | 3% | 1.25 |
| Ethanol* | — | 30 ml | — | 30 ml | — | 30 ml |
| Starlac | 85% | 34 | 91% | 36.5 | 94% | 37.75 |

*removed during the process
Starlac = Spray-dried compound consisting of 85% alpha-lactose monohydrate and 15% maize starch dry matter It was found during further formulation development that Starlac may be used. However, lactose, particularly agglomerated α-lactose-monohydrate [Ph.Eur./USP-NF/JP] (Tablettose®), results in additional advantages. The division of the polymer into two layers will achieve better coating efficiency at larger scales.

Example 3—Pharmaceutical Tablet Formulation Containing First Layer

Following the procedure according to example 1 pharmaceutical tablet formulations according to the present invention have been produced. The detailed compositions having only one layer (the first layer) coated on the carrier core particles are summarized in the following table 3 wherein different Eudragit® EPO: benazepril hydrochloride (E/B) ratios are used. The ACE inhibitor used is benazepril hydrochloride and the PDE III inhibitor used is pimobendan, however, any other instable ACE inhibitor and any other PDE III inhibitor may be used.

TABLE 3 tablet compositions

| | Dosage strength | | | |
|---|---|---|---|---|
| | 1.25/2.50 | 1.25/2.50 | 1.25/2.50 | |
| | | E/B ratio | | |
| | 01:05 | 2.5:1 | 1.25:1 | |
| | Tablet weight | | | |
| | 0.5 g | 0.5 g | 0.5 g | |
| Ingredients | mg/tablet | mg/tablet | mg/tablet | % |
| Benazepril hydrochloride | 2.50 | 2.50 | 2.50 | 0.91 |
| Eudragit ® EPO | 12.50 | 6.25 | 3.13 | 4.5/2.3/1.1 |
| Monohydrate lactose/starch | 150.00 | 156.25 | 159.37 | 54.3/56.6/57.7 |
| Pimobendan | 5.00 | 5.00 | 5.00 | 1.81 |
| Dry Meat Flavour | 50.00 | 50.00 | 50.00 | 18.12 |
| Colloidal silica, anhydrous | 2.50 | 2.50 | 2.50 | 0.91 |
| Maize starch, undried | 25.00 | 25.00 | 25.00 | 9.06 |
| Fumaric acid | 10.00 | 10.00 | 10.00 | 3.62 |
| Crospovidone | 10.00 | 10.00 | 10.00 | 3.62 |
| Iron oxide yellow | 6.00 | 6.00 | 6.00 | 2.17 |
| Stearic acid, micronized | 2.50 | 2.50 | 2.50 | 0.91 |
| Total amount per tablet | 276.00 | 276.00 | 276.00 | 100.00 |

II. Studies

1. Bioequivalence Study

The aim of this study was to assess the bioequivalence of coated benazepril tablets with Symrise flavour (manufactured by Delpharm) as test formulation against Fortekor® Flavour Tablets as reference for both the parent and the metabolite by evaluating the pharmacokinetic parameters of benazepril and its metabolite benazeprilate after single oral dosing at a dose level of 5 mg/dog.

Fortekor® Flavour Tablets (Novartis Animal Health UK Ltd.) are available on the market and contain the active substance benazepril hydrochloride at a dose level of 5 mg. The tablets are indicated for the treatment of heart failure in dogs.

The two different tablet formulations of benazepril were given to 12 female Beagle dogs (6 per group) in 2 different periods, in a (2×2) cross-over design. A wash-out period of 7 days was applied between the consecutive periods. Animals were fasted overnight prior to dosing and fed again 4 hours post-dose. Blood samples for pharmacokinetic purposes were collected at 0 (pre-dose), 0.25, 0.5, 1, 1.5, 2, 2.5, 3, 3.5, 4, 8 and 24 hours (h) after dosing. The samples were analyzed for benazepril and benazeprilate (metabolite) plasma concentrations.

For benazepril, bioequivalence of the coated benazepril tablets with Symrise flavour compared to the Fortekor® Flavour Tablets formulation could not be statistically demonstrated for $C_{max}$ and $AUC_{last}$. The limits of the 90% CI were outside the [80%, 125%] bioequivalence limits for $C_{max}$ and outside the upper bioequivalence limit for $AUC_{last}$. This was probably caused by an inadequate sampling size and/or high variability in $C_{max}$ and AUC-values observed in both treatment groups. No sequence, treatment or period effect was observed based on the calculated p-values (>0.05).

For benazeprilate, bioequivalence between both formulations was demonstrated for $AUC_{last}$. For $C_{max}$ bioequivalence could not be demonstrated because the upper value of the 90% CI was outside the 125% bioequivalence limit. No sequence, treatment or period effect was observed based on the p-values (>0.05).

These study results were compared with bioequivalence study results from a benazepril generic formulation. The high variability observed in the bioequivalence study was not seen in the study with the benazepril generic tablets.

2. Palatability Study

The objective of this study was to compare the palatability of Fortekor® Flavour tablets to the FDC test formulation (FDC formulation without pimobendan) in dogs. In this study the following parameters were determined:

Amount consumed (1=Complete consumption, 2=Partial consumption, 3=None)

Acceptance score (1=Immediate intake from bowl, 2=Hesitant intake from bowl >10 seconds, 3=Immediate intake from hand, 4=Hesitant intake from hand >10 seconds Time to consumption The study population consisted of 12 dogs (6 dogs per group) during the test phase (Study Day 1 to 24) during which each animal received either a Fortekor® Flavour 5 mg tablet (X) or a FDC benazepril 5 mg tablet (Y). The test phase consisted of three periods of six days, where the dogs received either test article X or Y, and a 3 day wash-out phase after period 1 and 2.

The dog which received in test period 1 the test article X received in period 2 article Y and in period 3 X again. The second group received Y in the first period, then X and again Y in the third period of the study.

Results:

The acceptance in dogs of the FDC test formulation is assessed to be comparable to the Fortekor® Flavour tablets in this study. One dog rejected the FDC formulation especially in phase 3 of the study.

The invention claimed is:

1. A pharmaceutical tablet formulation for the veterinary medical sector, the tablet formulation comprising:
a plurality of granules, wherein each granule comprises a plurality of carrier core particles, wherein each carrier core particle is coated with a first layer comprising a first pharmaceutically active substance and a coating and/or matrix forming polymer, the first pharmaceutically active substance comprising benazepril or a pharmaceutically acceptable salt thereof, and each carrier core particle coated with the first layer is further coated with a second layer comprising at least a coating and/or matrix forming polymer, the second layer being free of any pharmaceutically active substance; and
a tablet matrix within which the granules are embedded, wherein the tablet matrix comprises a second pharmaceutically active substance comprising pimobendan or a pharmaceutically acceptable salt thereof;
wherein the tablet formulation excludes citric acid and magnesium stearate.

2. The pharmaceutical tablet formulation of claim 1, wherein the carrier core particles of the granules are selected from the group consisting of lactose, carbohydrates, sugar alcohols, mannitol, sorbitol, maltitol, glucose, non-pareil-seeds, calcium phosphate, cellulose, microcrystalline cellulose (MCC), starch, spray dried lactose, agglomerated a-lactose-monohydrate, and mixtures thereof.

3. The pharmaceutical tablet formulation of claim 1, wherein the first pharmaceutically active substance is a pharmaceutically acceptable salt of benazepril, and the second pharmaceutically active substance is pimobendan.

4. The pharmaceutical tablet formulation of claim 2, wherein the coating and/or matrix forming polymer is a polymer on methacrylic acid basis.

5. The pharmaceutical tablet formulation of claim 2, wherein the ratio of the first pharmaceutically active substance to the at least one coating and/or matrix forming polymer in the first layer is from about 0.5 to 2:1 to 4.

6. The pharmaceutical tablet formulation of 1, wherein the ratio of the first pharmaceutically active substance to the at least one coating and/or matrix forming polymer in the first and second layers together is from about 0.5 to 2:4 to 16.

7. The pharmaceutical tablet formulation of claim 1, wherein one or both of the first and second layers further includes one or more excipients, and the excipients are selected from the group consisting of release modifying agents, binders, carriers, crystallization retarders, sweeteners, solubilizers, coloring agents, flavoring substances, pH control agents, taste masking agents, surfactants, anti-tacking agents, plasticizers, anti-static agents, and emulsifiers.

8. The pharmaceutical tablet formulation of claim 1, wherein the tablet matrix comprises one or more excipients, and the excipients are selected from the group consisting of binders, carriers, diluents, disintegrants, fillers, lubricants, acidifying agents, glidants, crystallization retarders, sweeteners, solubilizers, coloring agents, pH control agents, taste masking agents, anti-tacking agents, plasticizers, surfactants and emulsifiers.

9. The pharmaceutical tablet formulation of claim 1, wherein the ratio of granules (carrier core particles+first layer containing first pharmaceutically acceptable substance+second layer) to extra-granular material (tablet matrix+second pharmaceutically substance) is from 10:90 to 90:10 (w/w).

10. The pharmaceutical tablet formulation of claim 1, wherein the pharmaceutical tablet formulation is a chewable tablet.

11. A granule comprising:
a plurality of carrier core particles, wherein each carrier core particle is coated with a first layer comprising a first pharmaceutically active substance and a coating and/or matrix forming polymer, the first pharmaceutically active substance comprising benazepril or a pharmaceutically acceptable salt thereof, and each carrier core particle coated with the first layer is further coated with a second layer comprising at least a coating and/or matrix forming polymer, the second layer being free of any pharmaceutically active substance;
wherein the granule excludes citric acid and magnesium stearate.

12. The granules of claim 11, having a particle size distribution where ≥90% of the particles have a diameter of 125-750 μm and/or 50-80% of the particles have a diameter of 250-500 μm.

13. A process for preparing the pharmaceutical tablet formulation according to claim 1, comprising:

preparing a first fluid bed coating using a coating solution comprising benazepril or a pharmaceutically acceptable salt thereof and at least one coating and/or matrix forming polymer using carrier core particles to obtain a coated granulate;

preparing a second fluid bed coating using a further coating solution comprising at least one coating and/or matrix forming polymer to obtain a double coated granulate;

mixing pimobendan or a pharmaceutically acceptable salt thereof with the excipients of a tablet matrix to obtain a premix;

optionally sieving the obtained coated granulate through a screen;

mixing the coated granulate and the premix to obtain a blend;

mixing the blend with one or more lubricants and/or glidants to obtain a final blend, and compressing said final blend to a tablet.

14. The process of claim 13, wherein the fluid bed coating is a top-spray fluid bed process.

15. A method of treating heart diseases, disorders, or complications associated therewith, selected from the group consisting of heart failure, congestive heart failure, increased size of the heart, and hypertension in a mammal, in need thereof, comprising administration of the pharmaceutical tablet formulation of claim 1.

16. The pharmaceutical tablet formulation of claim 1, further comprising an organic acid disposed within the tablet matrix, wherein the organic acid is other than citric acid.

17. The pharmaceutical tablet formulation of claim 16, wherein the organic acid is selected from the group consisting of tartaric acid, malic acid and fumaric acid.

18. The pharmaceutical tablet formulation of claim 1, wherein the ratio of granules (carrier core particles+first layer containing first pharmaceutically acceptable substance+second layer) to extra-granular material (tablet matrix+second pharmaceutically substance) is from 20:80 to 80:20 (w/w).

19. The method of claim 15, wherein the method of treating is the treatment of congestive heart failure originating from dilated cardiomyopathy or valvular insufficiency.

20. The method of claim 15, wherein the method of treating is the treatment of congestive heart failure originating from mitral and/or tricuspid regurgitation.

21. The method of claim 15, wherein the mammal is a dog, a cat or a rodent.

\* \* \* \* \*

UNITED STATES PATENT AND TRADEMARK OFFICE
CERTIFICATE OF CORRECTION

PATENT NO. : 10,398,705 B2  
APPLICATION NO. : 14/384210  
DATED : September 3, 2019  
INVENTOR(S) : Folger et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 121 days.

Signed and Sealed this
Twenty-sixth Day of May, 2020

Andrei Iancu
*Director of the United States Patent and Trademark Office*